(12) United States Patent
Pipkin et al.

(10) Patent No.: US 8,829,182 B2
(45) Date of Patent: *Sep. 9, 2014

(54) SULFOALKYL ETHER CYCLODEXTRIN COMPOSITIONS AND METHODS OF PREPARATION THEREOF

(71) Applicant: CyDex Pharmaceuticals, Inc., La Jolla, CA (US)

(72) Inventors: James D. Pipkin, Lawrence, KS (US); Gerold L. Mosher, Kansas City, MO (US); Douglas B. Hecker, Liberty, MO (US)

(73) Assignee: Cydex Pharmaceuticals, Inc., Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,677

(22) Filed: Mar. 11, 2013

(65) Prior Publication Data

US 2013/0288054 A1  Oct. 31, 2013

Related U.S. Application Data

(63) Continuation of application No. 13/243,956, filed on Sep. 23, 2011, which is a continuation of application No. 12/108,228, filed on Apr. 23, 2008, now Pat. No. 8,049,003, which is a continuation of application No. PCT/US2005/038933, filed on Oct. 26, 2005.

(51) Int. Cl.
  *C08B 37/16* (2006.01)
  *B01D 1/18* (2006.01)

(52) U.S. Cl.
  CPC .............. *C08B 37/0012* (2013.01); *B01D 1/18* (2013.01)
  USPC ........................................................ 536/122

(58) Field of Classification Search
  None
  See application file for complete search history.

(56) References Cited

U.S. PATENT DOCUMENTS

| | | |
|---|---|---|
| 3,426,011 A | 2/1969 | Parmerter et al. |
| 4,199,578 A | 4/1980 | Stevenson |
| 4,738,923 A | 4/1988 | Ammeraal |
| 4,920,214 A | 4/1990 | Friedman |
| 4,946,654 A | 8/1990 | Uhlemann et al. |
| 5,024,998 A | 6/1991 | Bodor |
| 5,134,127 A | 7/1992 | Stella et al. |
| 5,241,059 A | 8/1993 | Yoshinaga |
| 5,284,133 A | 2/1994 | Burns et al. |
| 5,324,718 A | 6/1994 | Loftsson |
| 5,376,645 A | 12/1994 | Stella et al. |
| 5,393,880 A | 2/1995 | Shieh et al. |
| 5,437,271 A | 8/1995 | Hodson et al. |
| 5,469,843 A | 11/1995 | Hodson |
| 5,472,954 A | 12/1995 | Loftsson |
| 5,482,032 A | 1/1996 | Smith et al. |
| 5,518,998 A | 5/1996 | Backstrom et al. |
| 5,525,623 A | 6/1996 | Spear et al. |
| 5,569,756 A | 10/1996 | Qi et al. |
| 5,654,276 A | 8/1997 | Barrett et al. |
| 5,658,878 A | 8/1997 | Backstrom et al. |
| 5,668,110 A | 9/1997 | Barrett et al. |
| 5,674,854 A | 10/1997 | Bodley et al. |
| 5,677,280 A | 10/1997 | Barrett et al. |
| 5,683,983 A | 11/1997 | Barrett et al. |
| 5,691,336 A | 11/1997 | Dorn et al. |
| 5,724,959 A | 3/1998 | McAughey et al. |
| 5,750,549 A | 5/1998 | Caldwell et al. |
| 5,756,483 A | 5/1998 | Merkus |
| 5,756,484 A | 5/1998 | Fuertes et al. |
| 5,780,467 A | 7/1998 | Dorn et al. |
| 5,824,668 A | 10/1998 | Rubinfeld et al. |
| 5,846,954 A | 12/1998 | Joullie et al. |
| 5,863,554 A | 1/1999 | Illum |
| 5,874,418 A | 2/1999 | Stella et al. |
| 5,875,776 A | 3/1999 | Vaghefi |
| 5,877,191 A | 3/1999 | Caldwell et al. |
| 5,929,094 A | 7/1999 | Durette et al. |
| 5,935,939 A | 8/1999 | Kararli et al. |
| 5,935,940 A | 8/1999 | Weisz |
| 5,935,941 A | 8/1999 | Pitha |
| 5,942,251 A | 8/1999 | Merkus |
| 5,952,008 A | 9/1999 | Backstrom et al. |
| 5,955,454 A | 9/1999 | Merkus |
| 5,977,070 A | 11/1999 | Piazza et al. |
| 5,988,163 A | 11/1999 | Casper et al. |

(Continued)

FOREIGN PATENT DOCUMENTS

| | | |
|---|---|---|
| EP | 0 579 435 | 1/1994 |
| EP | 0 392 608 | 6/1995 |

(Continued)

OTHER PUBLICATIONS

Abdullah et al., 1999, The use of bulk density measurements as following indicators, Powder Technology, 102:151-165.

(Continued)

Primary Examiner — Eric S Olson
(74) Attorney, Agent, or Firm — Knobbe Martens Olson & Bear LLP

(57) ABSTRACT

A particulate SAE-CD composition is provided. The SAE-CD composition has an advantageous combination of physical properties not found in known solid forms of SAE-CD. In particular, the SAE-CD composition possesses an advantageous physicochemical and morphological property profile such that it can be tailored to particular uses. The SAE-CD composition of the invention has improved flow and dissolution performance as compared to known compositions of SAE-CD.

24 Claims, 4 Drawing Sheets

(56) References Cited

U.S. PATENT DOCUMENTS

| | | |
|---|---|---|
| 6,003,512 A | 12/1999 | Gerde |
| 6,022,737 A | 2/2000 | Niven et al. |
| 6,046,177 A | 4/2000 | Stella et al. |
| 6,077,871 A | 6/2000 | Campeta |
| 6,136,603 A | 10/2000 | Dean et al. |
| 6,138,673 A | 10/2000 | Shepherd |
| 6,153,746 A | 11/2000 | Shah et al. |
| 6,209,538 B1 | 4/2001 | Casper et al. |
| 6,258,341 B1 | 7/2001 | Foster et al. |
| 6,306,440 B1 | 10/2001 | Backstrom et al. |
| 6,309,671 B1 | 10/2001 | Foster et al. |
| 6,436,902 B1 | 8/2002 | Backstrom et al. |
| 6,479,049 B1 | 11/2002 | Platz et al. |
| 6,485,706 B1 | 11/2002 | McCoy et al. |
| 6,495,120 B2 | 12/2002 | McCoy et al. |
| 6,518,239 B1 | 2/2003 | Kuo et al. |
| 6,555,139 B2 | 4/2003 | Sharma |
| 6,559,122 B1 | 5/2003 | Oeswein et al. |
| 6,565,885 B1 | 5/2003 | Tarara et al. |
| 6,582,728 B1 | 6/2003 | Platz et al. |
| 6,589,560 B2 | 7/2003 | Foster et al. |
| 6,599,535 B2 | 7/2003 | Guitard et al. |
| 6,645,466 B1 | 11/2003 | Keller et al. |
| 6,673,335 B1 | 1/2004 | Platz et al. |
| 7,034,013 B2 | 4/2006 | Thompson et al. |
| 7,625,878 B2 | 12/2009 | Stella et al. |
| 7,629,331 B2 | 12/2009 | Pipkin et al. |
| 7,635,773 B2 | 12/2009 | Antle |
| 8,049,003 B2 | 11/2011 | Mosher et al. |
| 8,114,438 B2 | 2/2012 | Pipkin et al. |
| 2002/0071870 A1 | 6/2002 | Sharma |
| 2002/0117170 A1 | 8/2002 | Platz et al. |
| 2003/0028014 A1 | 2/2003 | Sikorski et al. |
| 2003/0055023 A1 | 3/2003 | Rajewski et al. |
| 2003/0059376 A1 | 3/2003 | Libbey et al. |
| 2003/0064928 A1 | 4/2003 | Backstrom et al. |
| 2003/0065167 A1 | 4/2003 | Lis et al. |
| 2003/0129139 A1 | 7/2003 | Batycky et al. |
| 2003/0138403 A1 | 7/2003 | Drustrup |
| 2003/0215512 A1 | 11/2003 | Foster et al. |
| 2003/0216353 A1 | 11/2003 | Mosher et al. |
| 2004/0234479 A1 | 11/2004 | Schleifenbaum et al. |
| 2005/0164986 A1 | 7/2005 | Mosher et al. |
| 2005/0187245 A1 | 8/2005 | Alnabari et al. |
| 2006/0128654 A1 | 6/2006 | Tang et al. |
| 2006/0194762 A1 | 8/2006 | Reer et al. |
| 2008/0075784 A1 | 3/2008 | Friesen et al. |
| 2010/0093663 A1 | 4/2010 | Antle |
| 2012/0136072 A1 | 5/2012 | Pipkin et al. |
| 2012/0164184 A1 | 6/2012 | Pipkin et al. |
| 2013/0197105 A1 | 8/2013 | Pipkin et al. |

FOREIGN PATENT DOCUMENTS

| | | |
|---|---|---|
| EP | 0 663 815 | 3/1999 |
| EP | 0 487 774 | 6/2002 |
| EP | 1 283 035 | 2/2003 |
| EP | 1 348 428 | 10/2003 |
| EP | 1 709 975 | 10/2006 |
| GB | 2 240 337 | 7/1991 |
| JP | 63-115820 | 5/1988 |
| JP | 63-115821 | 5/1988 |
| JP | 11-60610 | 3/1999 |
| JP | 11-171760 | 6/1999 |
| WO | WO 91/11172 | 8/1991 |
| WO | WO 94/02518 | 2/1994 |
| WO | WO 96/23485 | 8/1996 |
| WO | WO 98/50077 | 11/1998 |
| WO | WO 95/11666 | 5/1999 |
| WO | WO 99/42111 | 8/1999 |
| WO | WO 00/15262 | 3/2000 |
| WO | WO 00/66206 | 11/2000 |
| WO | WO 01/05429 | 1/2001 |
| WO | WO 01/40316 | 6/2001 |
| WO | WO 02/058735 | 8/2001 |
| WO | WO 01/78694 | 10/2001 |
| WO | WO 01/87278 | 11/2001 |
| WO | WO 02/056883 | 7/2002 |
| WO | WO 03/055511 | 7/2003 |
| WO | WO 03/055512 | 7/2003 |
| WO | WO 03/066031 | 8/2003 |
| WO | WO 03/079885 | 10/2003 |
| WO | WO 2004/017914 | 3/2004 |
| WO | WO 2005/004923 | 1/2005 |
| WO | WO 2005/023308 | 3/2005 |
| WO | WO 2005/042584 | 5/2005 |
| WO | WO2005/065435 * | 7/2005 |
| WO | WO 2005/065649 | 7/2005 |

OTHER PUBLICATIONS

Banks et al., 1991, Fluidised-bed granulation; a chronology, Drug Development and Industrial Pharmacy, 17(11):1437-1463.

Broadhead et al., 1992, The spray drying of pharmaceuticals, Drug Development and Industrial Pharmacy, 18(11-12):1169-1206.

Gereg et al., 2002, Roller compaction feasibility for new drug candidates: laboratory to production scale, Pharmaceutical Technology, pp. 14-23.

Hancock et al., Apr. 2003, The relative densities of pharmaceutical powders, blends, dry granulations, and immediate-release tablets, Pharmaceutical Technology, pp. 64-80.

Lin et al., 2003, Spray drying drop morphology: experimental study, Aerosol Science and Technology, 37:15-21.

Mathur, Fluid-Bed Dryers, Granulators and Coaters, in Encyclopedia of Pharmaceutical Technology, vol. 6, Swarbrick et al., eds., CRC Press, 1992, pp. 171-195.

Niro Inc., Feb. 2005, Fluid bed drying—fundamentals, 1 p.

Niro Inc., Feb. 2005, Spray drying & agglomeration, 2 pp.

US Pharmacopeia, 2012, (616) Bulk density and tapped density of powders, USP 36:265-268.

Office Action dated Jul. 21, 2010, in U.S. Appl. No. 11/550,976, Pipkin et al., filed Oct. 19, 2006.

Office Action dated Dec. 2, 2010, in U.S. Appl. No. 11/550,976, Pipkin et al., filed Oct. 19, 2006.

Adjei et al., Feb. 1992, Bioavailablity of leuprolide acetate following nasal and inhalation delivery to rats and healthy humans, Pharm. Res. 9(2):244-249.

Bayer Technology Services, Oct. 2005, Fluidized bed spray granulation, 2 pp.

Camoes et al., 2000, 27th Proceedings of the International Symposium on Controlled Release of Bioactive Materials, 794-795.

Captisol® Product Advantages, 1 p., 2002.

CyDex, 2002, Cyclopedia, 5(1):3.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Fukaya et al., 2003, A cyclosporin a/maltosyl-α-cyclodextrin complex for inhalation therapy of asthma, European Respiratory Journal, 22(2):213-219.

GEA Niro, 2008, Spray Drier Type MSD™ (Multi-Stage Drjer)/FSD™ (Fluidized Spray Drier) with integrated fluid bed, Product Brochure, 3 pp., downloaded from http://www.niro.com/niro/cmsdoc.nsf/webdocprint/webb7gmj9x, 3 pp.

GEA Process Engineering Inc., Fluid bed granulation, drying and coating, 3 pp.

Gudmundsdottir et al., Dec. 2001, Intranasal administration of midazolam in a cyclodextrin based formulation: bioavailability and clinical evaluation in humans, Pharmazie, 56(12):963-966.

Jain et al., 2001, Hygroscopicity, phase solubility and dissolution of various sulfobutylether beta-cyclodextrins and danasol-SBE inclusion complexes, International Journal of Pharmaceutics, 212(2):177-186.

(56) References Cited

OTHER PUBLICATIONS

Jin et al., Mar. 2008, Selected physical and chemical properties of feverfew (*Tanacetum parthenium*) extracts important for forumlated product quality and performance, AAPS PharmSciTech, 9(1):22-30.
Jung et al., 1996, Comparison of γ-cyclodextrin sulfobutyl ether and unmodified γ-cyclodextrin as chiral selectors in capillary electrophoresis, Journal of Chromatography, 755:81-88.
Kinnarinen et al., 2002, The in vitro pulmonary deposition of a budesonide/γ-cyclodextrin inclusion complex, Journal of Inclusion Phenomena and Macrocyclic Chemistry, 44:97-100.
Kinnarinen et al., 2003, Pulmonary deposition of a budesonide/γ-cyclodextrin complex in vitro, Journal of Controlled Release, 90(2):197-205.
Kobayashi et al., Jan. 1996, Pulmonary delivery of salmon calcitonin dry powders containing absorption enhancers in rats, Pharm. Res., 13(1):80-83.
Kristinsson et al., 1996, Dexamethasone-cyclodextrin-polymer co-complexes in aqueous eye drops, Investigative Ophthalmology & Visual Science, 37(6):1199-1203.
Kubota, 1975, Fluidized bed granulation method, Granulation Handbook, 1st ed., pp. 249-270 (partial translation pp. 253, 268).
Lammers et al., 1971, Properties of cyclodextrins: Part VI. Water-soluble cyclodextrin-derivatives. Preparation and Analysis, Die Starke, 23(5):167-171.
Lammers et al., 1972, Properties of cyclodextrins, Part VIII Determination of the composition of inclusion complexes of hexane and 2,3-dimethylbutane with cyclodextrin derivatives in aqueous solution, Recl. Tray. Chim. Pays-Bas, 91(6):733-753.
Lindley, 1991, Mixing processes for agricultural and food materials: 1. Fundamentals of mixing, J. Agric. Engng Res. 48:153-170.
Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.
Loftsson et al., 1994, The effect of water-soluble polymers on drug-cyclodextrin complexation, International Journal of Pharmaceutics (Netherlands), 110(2):169-177.
Loftsson et al., 1996, Effects of cyclodextrins and polymers on topical drug delivery to the eye—evaluations in humans, Proceedings of the 23rd International Symposium on Controlled Release of Bioactive Materials, pp. 453-454.
Loftsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, , 85(10):1017-1025.
Loftsson et al., Sep. 16, 1996, Drug-cyclodextrin-polymer ternary complexes, European Journal of Pharmaceutical Sciences, 4(SUPPL.):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug biovailability through addition of water-soluble polymers, Pharmazie, 53(11):733-740.
Luna et al., 1997, Fractionation and characterization of 4-sulfobutyl ether derivatives of cyclomaltoheptaose (β-cyclodextrin), Carbohydrate Research, 299:103-110.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Matsushita, 1995, Pharmaceutics I, Drug Preparation and Formulations, pp. 59-62 (partial translation pp. 60-61).
Modified Cyclodextrins: Scaffolds and Templates for Supramolecular Chemistry, Easton et al. eds., Imperial College Press, London, UK, 1999.
Mosher et al., 2000, Complexation and cyclodextrins, Encyclopaedia of Pharmaceutical Technology, pp. 49-87.
Muller et al., 1997, Budesonide microparticles for pulmonary delivery produced by supercritical carbon dioxide, Proceed. Int'l. Symp. Control. Rel. Bioact. Mater, 24:69-70.
Nachaegari et al., Jan. 2004, Coprocessed excipients for solid dosage forms, Pharmaceutical Technology, pp. 52-64.
Nakate et al., 2003, Comparison of the lung absorption of FK244 inhaled from a pressurized metered dose inhaler and a dry powder inhaler by healthy volunteers, European Journal of Pharmaceutics and Biopharmaceutics, 56(3):319-325.
Nakate et al., Mar. 2003, Improvement of pulmona absorption of cyclopeptide FK224 in rats by co-formulating with Eur. J. Pharm. Biopharm., 55(2):147-154.
New Trends in Cyclodextrins and Derivatives, Duchene ed., Editions de Sante, Parks, France, 1991.
Nimbalkar et al., 2001, Activation of diacetyldapsone and a preliminary evaluation of a cyclodextrin-diacetyldapsone complex in cultured lung cells, Biotechnol. Appl. Biochem. 33:123-125.
Pinto et al., 1999, Beclomethasone/cyclodextrin inclusion complex for dry powder inhalation, S.T.P. Pharma. Sciences, 9(3):253-256 (abstract).
Poly(ethylene glycol) Chemistry: Biotechnical and Biomedical Applications, Harris et., Plenum Press New York, 1992.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu et al., 2002, Sulfoalkyl ether β-cyclodextrin derivatives: synthesis and characterizations, J. Inclusion Phenom. Macro. Chem, 43:213-221.
Rajewski et al., 1996, Pharmaceutical applications of cyclodextrins. 2. In vivo drug delivery, J. Pharm. Sci. 85(11):1142-1169 (abstract).
Ramachandruni et al., May 2001, Design and validation of an annular shear cell for pharmaceutical powder testing, Journal of Pharmacetuical Sciences, 90(5):531-540.
Remington's Pharmaceutical Sciences, 18th Edition, Gennaro ed., 1990, Hydrophilic Dispersons, pp. 291-294.
Remy, Oct. 2010, Granular flow, segregation and agglomeraion in bladed mixers, dissertation for the degree of Doctor of Philosphy,

(56) References Cited

OTHER PUBLICATIONS

Graduate Program in Chemical and Biochemical Engineering, Rutgers, The State University of New Jersey, 285 pp.
Rodrigues et al., May 2003, The effect of cyclodextrins on the in vitro and in vivo properties of insulin-loaded (D,L-Lactic-Co-Glycolic Acid) microspheres, Artificial Organs, 27(5):492-497.
Sandler et al., Feb. 2010, Prediction of granule packing and flow behavior based on particle size and shape analysis, Journal of Pharmaceutical Sciences, 99(2):958-968.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Shao et al., 1994, Cyclodextrins as mucosal absorption promoters of insulin: III. Pulmonary route of delivery, Eur. J. Pharm. Biopharm. 40(5):283-288.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.
Smyth et al., 2004, Dynamic electrostatic charge determinations of dry powder blends for inhalation: correlations with dispersion performance, Respiratory Drug Delivery IX, pp. 805-808.
Smyth et al., 2004, Influence of physical form of Captisol® particles on performance as a dry powder aerosol carrier, Respiratory Drug Delivery IX, pp. 809-812.
Srichana et al., Jun. 2001, Cyclodextrin as a potential drug carrier in salbutamol dry powder aerosols: the in-vitro deposition and toxicity studies of the complexes, Respiratory Medicine, 96(6):513-519.
Staniforth et al., 1982, Interparticle forces in binary and ternary ordered powder mixes, J. Pharm Pharmacol. 34:141-145.
Stella, Mar. 31-Apr. 2, 1996, SBE7-β-CD, a new, novel and safe polyanionic β-cyclodextrin derivative: characterization and biomedical applications, Proceedings of the Eighth International Symposium on Cyclodextrins, Budapest, Hungary, pp. 471-476.
Szente et al., 1999, Highly soluble cyclodextrin derivatives: chemistry, properties, and trends in development, Advanced Drug Delivery Reviews 36:17-28.
Tarver et al., 2002, 2-*O*-substituted cyclodextrins as reversal agents for the neuromuscular blocker rocuronium bromide, Bioorganic & Medicinal Chemistry, 10:1819-1827.
Teunou et al., 1999, Effect of relative humidity and temperature on food powder flowability, Journal of Food Engineering, 42:109-116.
Third European Congress of Pharmaceutical Sciences, Edinburgh, Scotland, UK, Sep. 15-17, 1996.
Totterman et al., 1997, Intestinal safety of water-soluble β-Cyclodextrins in paediatric oral solutions of spironolactone: effects of human intestinal epithelial Caco-2 cells, J. Pharm. Pharmacol., 49:43-48.
Van der Kuy et al., Nov. 1999, Bioavailability of intranasal formulations of dihydroergotamine, Eur. J. Clin. Pharmacol., 55(9):667-680.
Vozone et al., 2003, Complexation of budesonide in cyclodextrins and particle aerodynamic characterization of the complex solid form for dry powder inhalation, Journal of Inclusion Phenomena and Macrocyclic Chemistry, 44(1-4):111-115 (abstract).
Williams et al., Mar. 1999, Influence of formulation technique for hydroxypropyl-β-cyclodextrin on the stability of aspirin in HFA 134a, Eur. J. Pharm. Biopharm, 47(2):145-152.
Worth et al., 1997, Steroid/cyclodextrin complexes for pulmonary delivery, Proceedings of the International Symposium on Controlled Release of Bioactive Materials, 24:747-748.
Office Action dated Sep. 10, 2010, in U.S. Appl. No. 12/108,228, Pipkin, J., et al., filed Apr. 23, 2008.
Accelerated Examination Support Document filed Jan. 31, 2009, in U.S. Appl. No. 12/363,719, Pipkin et al., filed Jan. 31, 2009.
Supplemental Accelerated Examination Support Document filed Sep. 11, 2009, in U.S. Appl. No. 12/363,719, Pipkin et al., filed Jan. 31, 2009.
Office Action dated May 15, 2009, in U.S. Appl. No. 12/363,719, Pipkin et al., filed Jan. 31, 2009.
Notice of opposition to a European patent, submitted by Strawman Limited in the Opposition to European Patent No. 1945228, dated Jan. 5, 2012, 17 pages.
Submission in opposition proceedings, submitted by CyDex Pharmaceuticals, Inc. in the Opposition to European Patent No. 1945228, dated Aug. 23, 2012, 30 pages.
International Search Report and Written Opinion dated Aug. 3, 2006 in PCT/US05/38933.
GEA Niro, 2014, Fluidized spray dryer FSD™ from GEA Niro, http://www.niro.com.niro,cmsdoc.nsf/WebDoc/ndkk5hmchfFluidizedSprayDryer, 3 pp.
GEA Niro, 2014, The MSD™ Multi-State Dryer for the Dairy Industry, http://www.niro.com/niro/cmsdoc.nsf/webdoc/webb7gmj9x, 3 pp.
Jain et al., Jan. 1, 2001, Hygroscopicity, phase solubility and dissolution of various sulfobutylether beta-cyclodextrins and danasol-SBE inclusion complexes, International Journal of Pharmaceutics, 212(2):177-186.
Li et al., 2004, Interparticle van der Weals force in powder flowability and compactibility, International Journal of Pharmaceutics, 280:77-93.
Polymer Science, in Physical Pharmacy. Physical Chemical Principles in Pharmaceutical Sciences, 4th edition, Martin et al., Lippincott Willliams & Wilkins, Baltimore, MD, 1993, pp. 446-450.
Ridgway et al., May 1, 1969, The effect of particle shape on powder properties, J. Pharm. Pharmac. 21, Suppl., pp. 30S-39S.
Sulfobutylether β-Cyclodextrin, in Pharmaceutical Excipients 2004: Single-user version, Rowe et al., eds., Pharmaceutical Press and American Pharmacists Association, 21 pp.
Thalberg et al., 2004, Comparison of different flowability tests for powders for inhalation, Powder Technology, 146:206-213.
United States Pharmacopeia, Jan. 1, 2005, (616) Bulk Density and Tapped Density, pp. 2379-2380.
Verhing, May 2008, Pharmaceutical particle engineering via spray drying, Pharmaceutical Research, 25(5):999-1022.
Office Action dated Jan. 16, 2014 in U.S. Appl. No. 13/243,956.

* cited by examiner

SULFOALKYL ETHER CYCLODEXTRIN COMPOSITIONS AND METHODS OF PREPARATION THEREOF

CROSS REFERENCE TO RELATED APPLICATIONS

This application is a continuation of U.S. application Ser. No. 13/243,956, filed Sep. 23, 2011, which is a continuation of U.S. application Ser. No. 12/108,228, filed Apr. 23, 2008, now U.S. Pat. No. 8,049,003, which is a continuation of International Application No. PCT/US2005/038933, filed Oct. 26, 2005, all of which are incorporated herein by reference in their entirety.

FIELD OF THE INVENTION

The present invention relates to sulfoalkyl ether cyclodextrin derivatives having improved physical properties and to methods of making the same.

BACKGROUND OF THE INVENTION

The non-chemical physical property profile of a composition can dramatically alter the in-process handling and performance, and possibly the in vitro or in vivo performance, of a particular material. In other words, a given chemical composition having a first physical property profile might be suitable for inhalation; whereas, the same chemical composition having a different second physical property profile might be unsuitable for inhalation. Likewise, a particular excipient having a first physical property profile might be better suitable for tabletting by compression than would be the same excipient having a different second physical property profile.

For example, the suitability of different physical forms of a material used as a carrier for dry powder inhalation will vary according to the non-chemical physical property profile of the various physical forms of the material. The delivery of a drug by inhalation allows for deposition of the drug in different sections of the respiratory tract, e.g., throat, trachea, bronchi and alveoli. Generally, the smaller the particle size, the longer the particle will remain suspended in air and the farther down the respiratory tract the drug can be delivered. Drugs are delivered by inhalation using a nebulizer, metered dose inhaler (MDI), or dry powder inhaler (DPI).

Dry powder inhalers provide powder pharmaceuticals in aerosol form to patients. In order to generate an aerosol, the powder in its static state must be fluidized and entrained into the patient's inspiratory airflow. The powder is subject to numerous cohesive and adhesive forces that must be overcome if it is to be dispersed. Fluidization and entrainment requires the input of energy to the static powder bed. The particle size, shape, surface morphology and chemical composition of carrier particles can influence aerosol dispersion. Increased drug dispersion and deposition is generally observed with smaller carrier size and increased proportion of fine particles. Elongated carriers generally increased aerosol dispersibility and drug FPF (fine particle fraction), possibly due to increased duration in the airstream drag forces. Carriers with smooth surfaces produced higher respirable fractions. Low respirable fractions were obtained from carriers with macroscopic surface roughness or smooth surfaces, whereas high respirable fractions were obtained from carriers with microscopic surface roughness, where smaller contact area and reduced drug adhesion occurred at the tiny surface protrusions. Thus for dry powder inhaler formulations, the size of carrier particles should be selected on the basis of a balance between these interrelated performance characteristics. Specifically, inter-particulate forces should be such that the drug particles adhere to the carrier (to aid in blending, uniformity, and allow the entrainment of drug into the inspiratory air-stream), yet also allow detachment of the fine drug particles from the surface of the coarser carrier particles so that delivery to the lung can be facilitated. In view of the above, different physical forms of the known solid carrier lactose may or may not be suitable for dry powder inhalation.

The same general impact of physical form upon excipient behavior is true for other pharmaceutical processes used to make dosage forms such as a tablet, liquid, suspension, emulsion, film, laminate, pellet, powder, bead, granule, suppository, ointment, cream, etc. In other words, a single excipient will need to be made in different physical forms in order for it to be better suited for particular uses. For improved tabletting by compression, for example, an excipient will preferably have improved flow. Good flow characteristics are desirable in order to facilitate handling and processing in a tablet press or capsule-filling machine. It will also have a compressibility within a particular range depending upon the role of the excipient in the tablet. If an excipient is going to be used in a constitutable liquid formulation, the excipient will preferably not clump when placed in the liquid and it will dissolve completely and quickly. Even though many of these are highly desired features in a solid excipient, it is very difficult to obtain any single excipient having all of these features. For this reason, among others, many different grades of excipients are developed in the pharmaceutical industry.

Drying methods such as tray drying, freeze drying, spray drying, fluidized bed spray granulation, and fluidized bed spray agglomeration, among others, are used in the pharmaceutical industry to prepare solids from feed solutions, emulsions, suspensions or slurries. The physical properties of the isolated solid will depend upon the properties of the feed material and the parameters employed in and the equipment used for the drying method employed.

Spray drying entails atomizing a solids-containing feed solution or suspension to form atomized droplets directed into a stream of hot gas in a drying chamber thereby evaporating the liquid carrier from the droplets resulting in the formation of spherical particles. Fluidized bed spray drying is a modified form of spray drying wherein a spray drying process is performed in the presence of a fluidized bed (fluidized by the stream of hot gas) of fine particles such that the atomized droplets collide with and adhere to the fluidized particles. By modifying the solids content of the feed solution and in the drying chamber, a spray drying apparatus can be made to agglomerate or granulate the solids in a process called fluidized bed spray agglomeration or fluidized bed spray granulation, respectively. Moreover, the use of a rectangular versus cylindrical spray drying apparatus will have an impact upon the physical properties of the resulting product.

In an exemplary fluidized bed spray agglomeration/granulation with a cylindrical apparatus, powder feed enters the solids feed inlet at a controllable speed, and the liquid spray system sprays liquid feed from the top or bottom of the fluidized bed into the material. Heated fluidizing gas flows upward from the inlet through the bottom screen, fluidizing the powder feed or seed particles in the fluidized-bed chamber. Simultaneously, classifying gas flows upward through the discharge pipe at a velocity that's controlled to blow fine particles back into the fluidized bed, allowing only larger particles with a falling velocity higher than the discharge pipe's classifying air velocity to discharge through the pipe. This allows control of the product's particle size while keeping the product dust-free. Dust removed from the exhaust air by the circular unit's external dedusting equipment can be recirculated to the recycle inlet for further processing. During this process, the smaller particles fuse with each other or with larger particles to form agglomerates. As a result, the particle size distribution of the particles in the fluidized bed increases such that the percentage of fine particles present in the product is reduced as compared to the fluidized feed material.

Solubilization of poorly water soluble compounds in aqueous media is often very difficult. Therefore, artisans have employed solubilization enhancers, such as cyclodextrins, in the aqueous medium. Parent (underivatized) cyclodextrins and their derivatives are well known excipients that contain 6, 7, or 8 glucopyranose units and are referred to as α-, β-, and γ-cyclodextrin, respectively. Each cyclodextrin subunit has secondary hydroxyl groups at the 2 and 3 positions and a primary hydroxyl group at the 6-position. The cyclodextrins may be pictured as hollow truncated cones with hydrophilic exterior surfaces and hydrophobic interior cavities.

β-CD has been reportedly prepared in a variety of different forms using different finishing processes. American Maize Products (French patent No. 2,597,485) recommends freeze-drying and spraying as suitable methods for recovering cyclodextrin ethers from aqueous solutions. However, the powders obtained according to these various techniques have poor dissolution. In addition, these powders do not flow easily and possess mediocre compression properties.

U.S. Pat. No. 6,555,139 to Sharma discloses a method for microfluidizing β-CD in combination with a hydrophobic drug to yield a smooth, latex-like microsuspension.

U.S. Pat. No. 5,674,854 to Bodley et al. discloses a composition containing an inclusion complex of β-CD and diclofenac. The composition can be prepared by spray agglomeration.

U.S. Patent Application Publication No. 20040234479 to Schleifenbaum discloses a flavor or fragrance containing a cyclodextrin particle containing the cyclodextrin particle and a flavor or fragrance, wherein the cyclodextrin particle has a particle size in a range of 50 to 1000μ. The cyclodextrin particle comprises a cellulose ether and cyclodextrin, wherein the cyclodextrin particle is obtained by a single stage fluidized bed process from a spray mixture, and wherein a gas introduction temperature is from 80° to 180° C. and a gas outlet temperature is from 40° to 95° C.

European Patent Application No. EP 392 608 describes a method for producing powdered cyclodextrin complexes wherein the particle size is less than 12μ, preferably less than 5μ. Suitable processes for doing so include spray-drying and freeze-drying. The '608 application states that small particle sizes of CD often exhibit reduced pourability or flowability and may dust easily. For this reason, the art suggests the use of cyclodextrin complex particles having particle sizes of at least 50μ.

U.S. Patent Application Publication No. 20030065167 to Lis et al. discloses a process for preparing a directly compressible β-CD. The process includes "a step of dehydrating hydrated beta-cyclodextrin to a water content of less than 6%, preferably less than 4% and more preferably still less than or equal to 2% by weight, followed by forced rehydration to a water content greater than 10%, preferably greater than 12% and more preferably still greater than or equal to 13% by weight.

The impact of the drying step or finishing step in the preparation of hydroxypropyl-β-cyclodextrin (HP-β-CD) obtained from a syrup containing the same has been explored. U.S. Patent Application Publication No. 20030028014 to Sikorski et al. discloses an agglomerated HP-β-CD and a process from making the same. The agglomerated product is made in a double drum dryer. It reportedly has low dusting and good dissolution in water. The particle size of the product is about 30 to 200μ.

U.S. Pat. No. 5,756,484 to Fuertes et al. discloses a pulverulent HP-β-CD composition and a method for its preparation. The HP-β-CD has a centered particle size free of fine particles and an appreciably improved capacity to dissolve in aqueous medium. The HP-β-CD is made by spraying a solution of HP-β-CD on a moving pulverulent bed of HP-β-CD particles.

The physical and chemical properties of the parent cyclodextrins can be modified by derivatizing the hydroxyl groups with other functional groups. One such derivative is a sulfoalkyl ether cyclodextrin.

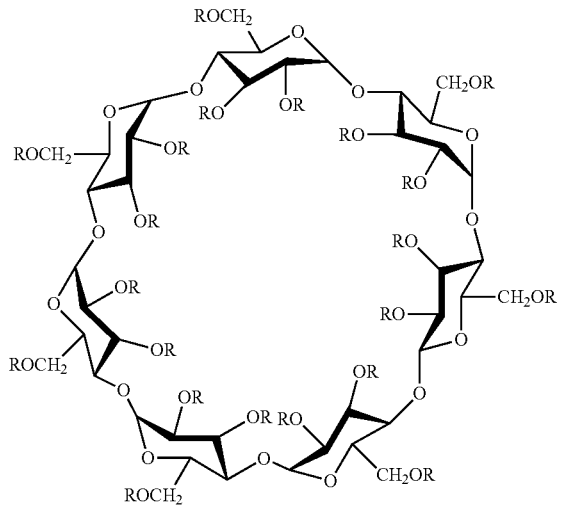

Sulfobutyl Ether-β-Cyclodextrin (Captisol ®)
R = (—H)$_{21-n}$ or (—(CH$_2$)$_4$—SO$_3$Na)$_n$ where n = 6.0-7.1

Sulfoalkyl ether cyclodextrin (SAE-CD) derivatives are well known as are their uses in a wide range of applications. SAE-CD derivatives are particularly useful in solubilizing and/or stabilizing drugs. A sulfobutyl ether derivative of beta cyclodextrin (SBE-β-CD), in particular the derivative with an average of about 7 substituents per cyclodextrin molecule (SBE7-β-CD), has been commercialized by CyDex, Inc. as CAPTISOL®. The anionic sulfobutyl ether substituent dramatically improves the aqueous solubility of the parent cyclodextrin. In addition, the presence of the charges decreases the ability of the molecule to complex with cholesterol as compared to the hydroxypropyl derivative. Reversible, non-covalent, complexation of drugs with CAPTISOL® cyclodextrin generally allows for increased solubility and stability of drugs in aqueous solutions.

CAPTISOL®, prepared by spray drying, is used in the commercial formulations VFEND® and GEODON®. It has become a leading cyclodextrin derivative for use in pharmaceutical formulations and thus is important to the industry.

Methods of preparing SAE-CD derivatives are varied but generally include the general steps of sulfoalkylation followed by isolation. The chemical property profile of the SAE-CD is established during the sulfoalkylation step. For example, altering reaction conditions during sulfoalkylation can vary the average degree of substitution for and the average regiochemical distribution of sulfoalkyl groups in the SAE- CD. The alkyl chain length of the sulfoalkyl functional group is determined according the sulfoalkylating agent used. And use of a particular alkalizing agent during alkylation would result in formation of a particular SAE-CD salt, unless an ion exchange step were performed subsequent to sulfoalkylation.

In general, known processes for the sulfoalkylation step include, for example: 1) exposure of underivatized parent cyclodextrin under alkaline conditions to an alkylating agent, e.g. alkyl sultone or a haloalkylsulfonate; 2) optional addition of further alkalizing agent to the reaction milieu to consume excess alkylating agent; and 3) neutralization of the reaction medium with acidifying agent. The vast majority of literature processes conduct the sulfoalkylation step in aqueous media; however, some references disclose the use of pyridine, dioxane, or DMSO as the reaction solvent for sulfoalkylation. Literature discloses the use of an alkalizing agent in order to accelerate the sulfoalkylation reaction. Upon completion of the sulfoalkylation step, isolation and purification of the SAE-CD is conducted.

Several different isolation processes for SAE-CD following sulfoalkylation and neutralization are described. In general, an aqueous liquid containing SAE-CD is dried to remove water to form a solid. The literature suggests various methods for removal of water from an aqueous solution containing SAE-CD. Such methods include conventional freeze-drying, spray drying, oven drying, vacuum oven drying, roto-evaporation under reduced pressure, vacuum drying or vacuum drum drying. See, for example, Ma (*S.T.P. Pharma. Sciences* (1999), 9(3), 261-266), CAPTISOL® (sulfobutyl ether beta-cyclodextrin sodium; *Pharmaceutical Excipients* 2004; Eds. R. C. Rowe, P. J. Sheskey, S. C. Owen; Pharmaceutical Press and American Pharmaceutical Association, 2004) and other references regarding the preparation of SAE-CD derivatives.

The art, therefore, is lacking teaching on the methods of preparing and using SAE-CD derivatives having particular non-chemical physical property profiles. Given the importance of SAE-CD to the pharmaceutical industry, it would be a significant improvement in the art to provide SAE-CD derivatives having particular non-chemical physical property profiles so that such forms can be tailored for particular purposes.

SUMMARY OF THE INVENTION

The present invention seeks to overcome the disadvantages present in known dry powder compositions of SAE-CD. As such, a derivatized cyclodextrin-based, e.g., sulfoalkyl ether cyclodextrin (SAE-CD)-based, composition is provided. The present SAE-CD composition excludes a principal active agent. However, the composition possesses unexpectedly advantageous physical properties that exist as a result of the method used to remove water from an aqueous medium containing SAE-CD. The composition prepared by the process of the invention provides solid SAE-CD in particulate form.

The physical properties of the SAE-CD are modulated through a variety of techniques to yield different grades of SAE-CD (a SAE-CD grade or SAE-CD composition) wherein each is adapted for use in specific dosage forms, such as a tablet, capsule, constitutable powder, dry powder inhaler, sache, troche, and lozenge. The properties can also be modified for improved handling, packaging, storage and other process related activities. Also, the chemical properties can be adapted for particular uses by changing the identity of the counterion, changing the alkyl chain length, average degree of substitution, or ring size of the parent cyclodextrin from which the SAE-CD is made. The properties can also be adapted for particular uses by changing the non-chemical physical properties of the SAE-CD such as by changing the mean or average particle diameter, the span of the particles size distribution, the water content of the SAE-CD, the surface characteristics of the SAE-CD particles, the rate of dissolution of the particles, the bulk density, the tap density, the Carr Index, compressibility, flowability and more.

The SAE-CD compositions of the invention possess numerous advantages over known compositions of SAE-CD, i.e., those prepared according to known methods that differ in the post-sulfoalkylation steps. The SAE-CD compositions herein provide an unexpectedly improved aqueous dissolution rate, compression crushing strength, ease of tabletting, and/or improved solids handling.

One form of a SAE-CD composition is provided containing no more than about 20% by wt. moisture. The SAE-CD composition can be included in a dry formulation in admixture with an active agent such that all or substantially all of the active agent is not complexed with the SAE-CD. The SAE-CD composition can be included in a dry formulation in admixture with one or more excipients. The SAE-CD composition can also be included in a constitutable formulation.

The particulate SAE-CD compositions of the invention possess morphological and physicochemical properties that predispose them to dissolve more rapidly than previously known compositions of SAE-CD such as those prepared by spray drying. The SAE-CD compositions, prepared by the processes described herein, possess particular combinations of morphological and physicochemical properties. In some embodiments, the process is fluidized bed spray agglomeration. In some embodiments, the particulate SAE-CD composition is prepared by fluidized bed spray granulation, and the resulting SAE-CD composition possesses a different combination of physical properties than does a SAE-CD composition prepared by fluidized bed spray agglomeration.

When SAE-CD particles are prepared by known methods, they do not possess the advantageous combination of physical properties as that found in the SAE-CD composition of the invention. A SAE-CD composition disclosed herein is prepared by a process comprising:

providing an aqueous liquid feed comprising water and SAE-CD; and subjecting the liquid feed to a combination fluidized bed spray drying process whereby the SAE-CD is agglomerated (and/or granulated) and dried to below the point of deliquescence to form a particulate SAE-CD composition comprising agglomerated (and/or granulated) particles wherein at least 90% of the particle volume of the SAE-CD composition is made of particles having calculated diameters greater than or equal to about 25 microns. (The particle diameter cut-off for the 10% cumulative volume fraction is 25 microns or greater.) The SAE-CD composition can possess a tapped density in the range of about 0.66 to 0.75 g/cm$^3$ or about 0.49 to 0.75 g/cm$^3$ when determined according to USP <616> Method 1 and/or a bulk density in the range of about 0.55 to 0.66 g/cm$^3$ or about 0.38 to about 0.66 g/cm$^3$ when determined according to USP <616> Method 1. For a specific SAE-CD composition, the tapped density is higher than the bulk density.

The moisture content of the SAE-CD composition is below its point of deliquescence. However, particular embodiments include those having a moisture content of ≤18% by wt., ≤16% by wt., ≤15% by wt., ≤10% by wt., or 5% by wt.

The SAE-CD composition is particulate and has a mean particle diameter of about 92 to about 200 microns, or less than or equal to about 110 microns, or less than or equal to about 200 microns. The mean particle diameter has been determined according to Example 3 with a Malvern instrument. This instrument measures particle diameter via low angle laser light scattering and calculates particle diameter based upon the volume of an assumed spherical shape. The term "mean particle diameter" is defined as the volume moment mean, otherwise known as the De Brouckere mean diameter, D[4,3]. The SAE-CD composition can be prepared by fluidized bed spray agglomeration or fluidized bed spray granulation.

The SAE-CD composition has a combination of physical properties that render it better suited than previously known SAE-CD compositions for use in compressed tablet formulations. For example, the SAE-CD composition has a compression crushing strength in the range of about 1.0 to about 20 kP when 200 mg of SAE-CD composition are compressed into a tablet having a diameter of 0.345 inches using a Pmax (peak compression pressure) in the range of about 30 to about 275 MPa and the SAE-CD composition has a moisture content in the range of about 2 to about 3% by wt. as determined by LOD. Alternatively, the SAE-CD composition has a compression crushing strength in the range of about 0.5 to 11 KP when 200 mg of SAE-CD composition are compressed into a tablet having a diameter of 0.345 inches using a Pmax MPa in the range of about 15-70 MPa and the SAE-CD has a moisture content in the range of about 5-6% by wt.

The SAE-CD composition possesses a more rapid dissolution rate in water than does SAE-CD prepared by conventional spray drying. When 2.5 g of SAE-CD composition is assayed according to Example 6, it has an average dissolution time of 2.5 minutes or less, or 4.5 minutes or less, or 3.5 minutes or less when placed in water.

A SAE-CD composition having an advantageous flow property is provided by the invention. For example, the SAE-CD composition has a gravitational-flow minimum orifice diameter of about 3-7 mm or 4-6 mm, or less than about 10 mm or less than about 20 mm. The method of Example 5 can be followed to determine the gravitational-flow minimum orifice diameter.

Density of the SAE-CD composition can be controlled. The SAE-CD composition has a true density of 1.25 to 1.35 g/cm$^3$ or 1.1 to 1.5 g/cm$^3$. Embodiments of the SAE-CD composition include those having a bulk density of about 0.55 to about 0.66 g/cm$^3$, about 0.38 to less than about 0.55 g/cm$^3$, or about 0.38 to about 0.66 g/cm$^3$ when performed according to USP <616> Method 1. Other embodiments have a tap density (tapped density) of about 0.66 to about 0.75 g/cm$^3$, or about 0.49 to about 0.66 g/cm$^3$ or about 0.49 to about 0.75 g/cm$^3$ when performed according to USP <616> Method 1. Additionally or alternatively, the SAE-CD composition has a CARR's index of less than or about 24% or less than or about 18% or less than or about 16%.

Another aspect of the invention provides a SAE-CD composition having a moisture content below its point of deliquescence, a bulk density in the range of about 0.55 to 0.66 g/cm$^3$, and a tapped density in the range of about 0.66 to 0.75 g/cm$^3$, a CARR's index of less than or about 24%; and optionally, a moisture content of less than about 18% by wt., optionally a true density in the range of about 1.1 to 1.5 g/cm$^3$, optionally a gravitational-flow minimum orifice diameter of less than about 20 mm, optionally, wherein the SAE-CD composition is prepared by fluidized bed spray agglomeration or fluidized bed spray granulation.

Another aspect provides for the use of the SAE-CD compositions as tabletting excipients, capsule excipients, DPI (dry powder inhaler) excipients, extrusion excipients, PMDI (pressurized metered dose inhaler) excipients, carriers for delivery of a drug via a DPI or PMDI, orodispersible tablet excipients, ingestible powders, dry granulation excipients, pelletizing excipients, non-pariel seeds, aerosolizable powders, and/or constitutable powder excipients.

The SAE-CD composition can be included in a formulation (e.g. solid, liquid, gel, suspension, emulsion, or other known formulation) comprising one or more active agents and, optionally, one or more excipients. Therefor, the invention also provides a method of treating diseases or disorders by administration to a subject of the SAE-CD composition in a formulation further comprising an active agent.

In one embodiment, the properties of the SAE-CD composition can be modulated such that different physicochemical properties are matched to drug particle properties for optimizing dispersion from dry powder inhalers.

Additional embodiments of the invention include those wherein: 1) the SAE-CD composition is a compound of the formula 1 or a mixture thereof; 2) a formulation containing the SAE-CD composition further comprises an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, or a combination thereof; and/or 3) the SAE-CD is a compound of the formula 2 or a mixture thereof.

Another aspect of the invention provides an improved solid formulation, the improvement comprising including in the formulation a SAE-CD composition of the invention, wherein the SAE-CD has been prepared by a fluidized bed spray drying process (agglomeration or granulation) or a SAE-CD composition possessing a physical property profile as defined herein. These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

DETAILED DESCRIPTION OF THE INVENTION

Figure 1:
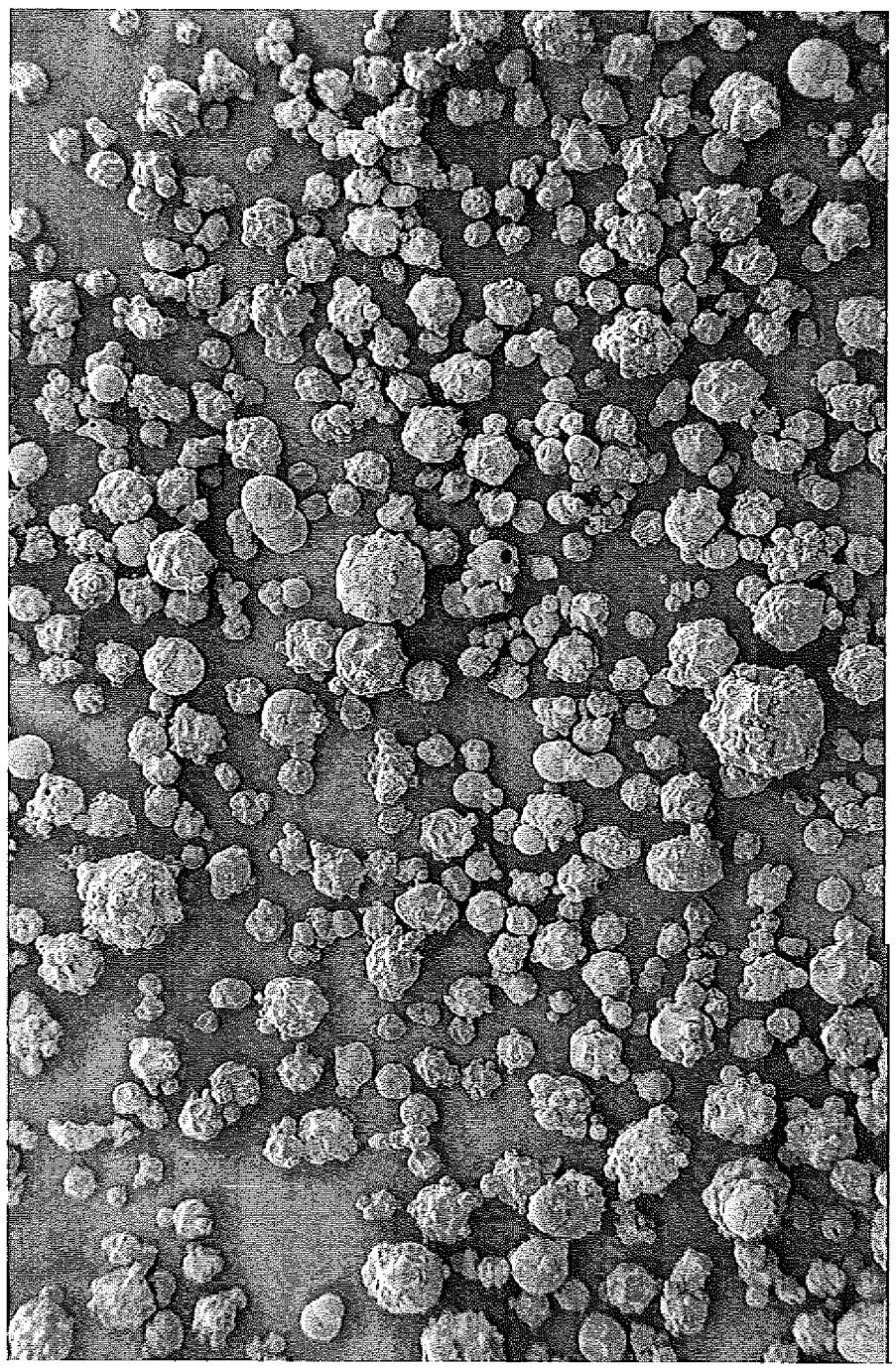
FIG. 1 depicts a SEM (scanning electron microscope) photograph of an exemplary batch of SAE-CD composition made according to the invention. The SAE-CD particles were made according to different post-sulfoalkylation processes.

The compositions of SAE-CD are adapted for use in particular applications. When used in those applications, the present compositions of SAE-CD are advantageous over and provide improved performance over previously known compositions of SAE-CD for those applications. By varying the finishing conditions (post-sulfoalkylation steps; steps occurring subsequent to the sulfoalkylation step), one is able to modify the physicochemical and morphological properties of the SAE-CD. For example, different SAE-CD compositions can be obtained by varying the drying and isolation conditions.

Even though the SAE-CD composition of the invention does not require attritting, it can be attritted to provide even further modified SAE-CD compositions. For example, attritting an SAE-CD composition prepared by fluidized bed spray drying can result in an SAE-CD composition having a different bulk density, tapped density, and/or particle diameter. As used herein, the term attritting means to physically abrade a solid to reduce its particle size. Any such process used in the pharmaceutical industry is suitable for use in the process of the invention. Attrition processes include, by way of example and without limitation, micronizing, ball milling, jet milling, hammer milling, pin milling, tumbling, sieving, and mortar and pestle. Both low and high energy methods can be used.

The present invention provides a "SAE-CD composition", meaning a composition of sulfoalkyl ether cyclodextrin having a combination of different physical properties and excluding an active agent or pharmaceutical excipient. As regards the SAE-CD composition, the term "excluding" means not purposefully added. Therefore, it is possible for the SAE-CD composition to contain excipients endogenous to its method of manufacture. For example, a first SAE-CD composition will have a first combination of physical properties, i.e. a first physical property profile, and the second SAE-CD composition will have a second combination of physical properties. By virtue of the different combinations of physical properties, the first SAE-CD composition will be more advantageous for a particular use, and the second SAE-CD composition will be more advantageous for another particular use.

The present invention provides SAE-CD compositions, wherein the SAE-CD is a compound of the Formula 1, or a combination thereof:

Formula 1

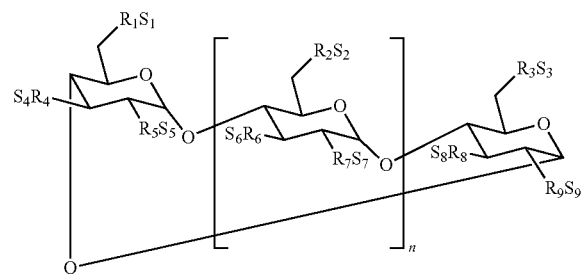

wherein:

n is 4, 5 or 6;

$R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ to $R_9$ is independently a —O—($C_2$-$C_6$ alkylene)-$SO_3^-$ group, preferably a —O—$(CH_2)_m SO_3^-$ group, wherein m is 2 to 6, preferably 2 to 4, (e.g. —$OCH_2CH_2CH_2SO_3^-$ or —$OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$, alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

Suitable methods for preparing a SAE-CD raw material for use in preparing the SAE-CD composition of the invention are disclosed U.S. Pat. No. 5,376,645, No. 5,874,418, and No. 5,134,127 to Stella et al.; U.S. Pat. No. 3,426,011 to Parmerter et al.; Lammers et al. (*Recl. Tray. Chim. Pays-Bas* (1972), 91(6), 733-742); *Staerke* (1971), 23(5), 167-171); Qu et al. (*J. Inclusion Phenom. Macro. Chem.*, (2002), 43, 213-221); U.S. Pat. No. 5,241,059 to Yoshinaga; U.S. Pat. No. 6,153,746 to Shah; PCT International Publication No. WO 2005/042584 to Stella et al.; Adam et al. (*J. Med. Chem.* (2002), 45, 1806-1816); PCT International Publication No. WO 01/40316 to Zhang et al.; Tarver et al. (*Bioorganic & Medicinal Chemistry* (2002), 10, 1819-1827); Ma (*S.T.P. Pharma. Sciences* (1999), 9(3), 261-266); Jung et al. (*J. Chromat.* 1996, 755, 81-88); and Luna et al. (*Carbohydr. Res.* 1997, 299, 103-110), the entire disclosures of which are hereby incorporated by reference.

The SAE-CD raw material is included in the liquid feed used in the fluidized bed spray drying process employed to prepare an SAE-CD composition of the invention.

The SAE-CD composition of the invention can also include a combination of derivatized cyclodextrin (SAE-CD) and underivatized cyclodextrin. For example, a SAE-CD composition can be made to include underivatized cyclodextrin in the amount of 0 to less than 50% by wt. of the total cyclodextrin present. Exemplary embodiments of the SAE-CD composition include those comprising 0-5% by wt., 5-50% by wt., less than 5%, less than 10%, less than 20%, less than 30%, less than 40%, or less than 50% underivatized cyclodextrin.

The terms "alkylene" and "alkyl," as used herein (e.g., in the —O—($C_2$-$C_6$-alkylene)$SO_3^-$ group or in the alkylamines), include linear, cyclic, or branched, and saturated or unsaturated (i.e., containing one double bond) divalent alkylene groups or monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl)cyclic alcohols.

Some embodiments of the present invention provide compositions containing a single type of cyclodextrin derivative having the structure set out in formula (I), where the composition overall contains on the average at least 1 and up to 3n+6 alkylsulfonic acid moieties per cyclodextrin molecule. The invention also includes compositions containing cyclodextrin derivatives having a narrow or wide range for degree of substitution and high or low degree of substitution. These combinations can be optimized as needed to provide cyclodextrins having particular properties.

Exemplary SAE-CD derivatives include SBE4-β-CD, SBE7-β-CD, SBE11-β-CD, SBE7-γ-CD and SBE5-γ-CD which correspond to SAE-CD derivatives of the formula I wherein n=5, 5, 5, 6 and 6, respectively; m is 4; and there are on average 4, 7, 11, 7 and 5 sulfoalkyl ether substituents present, respectively. Other exemplary SAE-CD derivatives include those of the formula SAEx-R-CD (Formula 2), wherein SAE is sulfomethyl ether (SME), sulfoethyl ether (SEE), sulfopropyl ether (SPE), sulfobutyl ether (SBE), sulfopentyl ether (SPtE), or sulfohexyl ether (SHE); x (average or specific degree of substitution) is 1-18, 1-21, 1-24, when R (ring structure of parent cyclodextrin) is α, β or γ, respectively; and CD is cyclodextrin. The SAE functional group includes a cationic counterion as disclosed herein or generally as used in the pharmaceutical industry for the counterion of any acidic group.

Since SAE-CD is a poly-anionic cyclodextrin, it can be provided in different salt forms. Suitable counterions for the SAE functional group(s) include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater electrostatic charge than a different second salt form of SAE-CD. The calcium salt form has been found to be more electronegative than the sodium salt form. Likewise, a SAE-CD having a first degree of substitution can have a greater electrostatic charge than a second SAE-CD having a different degree of substitution.

When the SAE-CD composition is intended for intra-pulmonary administration, the median particle diameter can be in the range of about 0.1 to about 10 microns or about 0.5 to about 6.4 microns. If it is desired that the particles reach the lower regions of the respiratory tract, i.e., the alveoli and terminal bronchi, the median particle diameter size range can be in the range of about 0.5 to about 2.5 microns. If it is desired that the particles reach the upper respiratory tract, the particle diameter size range can be between 2.5 microns and 10 microns. A SAE-CD composition with this median particle diameter size can be prepared by attritting a SAE-CD composition having a larger median particle diameter size range.

The particle diameter span (defined as the ratio=(mean particle diameter of the $90^{th}$ percentile−mean particle diameter of $10^{th}$ percentile)/mean particle diameter of the $50^{th}$ percentile) of the SAE-CD composition can also impact its performance. SAE-CD having broad, moderate and narrow particle size distribution may be used in the invention. A larger span indicates a broader particle size distribution and a smaller span indicates a narrower particle size distribution. Specific embodiments include those wherein the span is in the range of about 1.5 to 2.9, 1.1 to 1.9, or 1.4 to 1.7.

Since particles are present as a distribution of sizes, the distribution can be monomodal, bimodal or polymodal, the preferred being monomodal distribution.

The SAE-CD composition is a particulate composition containing agglomerated and non-agglomerated particles. Agglomerated particles can be prepared by fluidized bed spray drying, which can include agglomeration and/or granulation. The term agglomeration, which can be used interchangeably with granulation, is taken to mean a process in which dispersed fine particles in a composition are fused with other particles in the composition to form a coarser particulate composition thereby reducing the amount of fine particles and increasing the overall mean particle diameter of the composition. The collection of particles that results can be called an agglomerate or granulate. The SAE-CD composition of the invention is distinguishable by SEM from other compositions of SAE-CD made according to other processes. FIG. 1 depicts a SEM of an exemplary SAE-CD composition made by fluidized bed spray drying. The particles have a rough surface texture and comprise a substantial amount of agglomerated particles.

Exemplary processes for the preparation of the SAE-CD composition include fluidized bed spray agglomeration or fluidized bed spray granulation.

Figure 2:
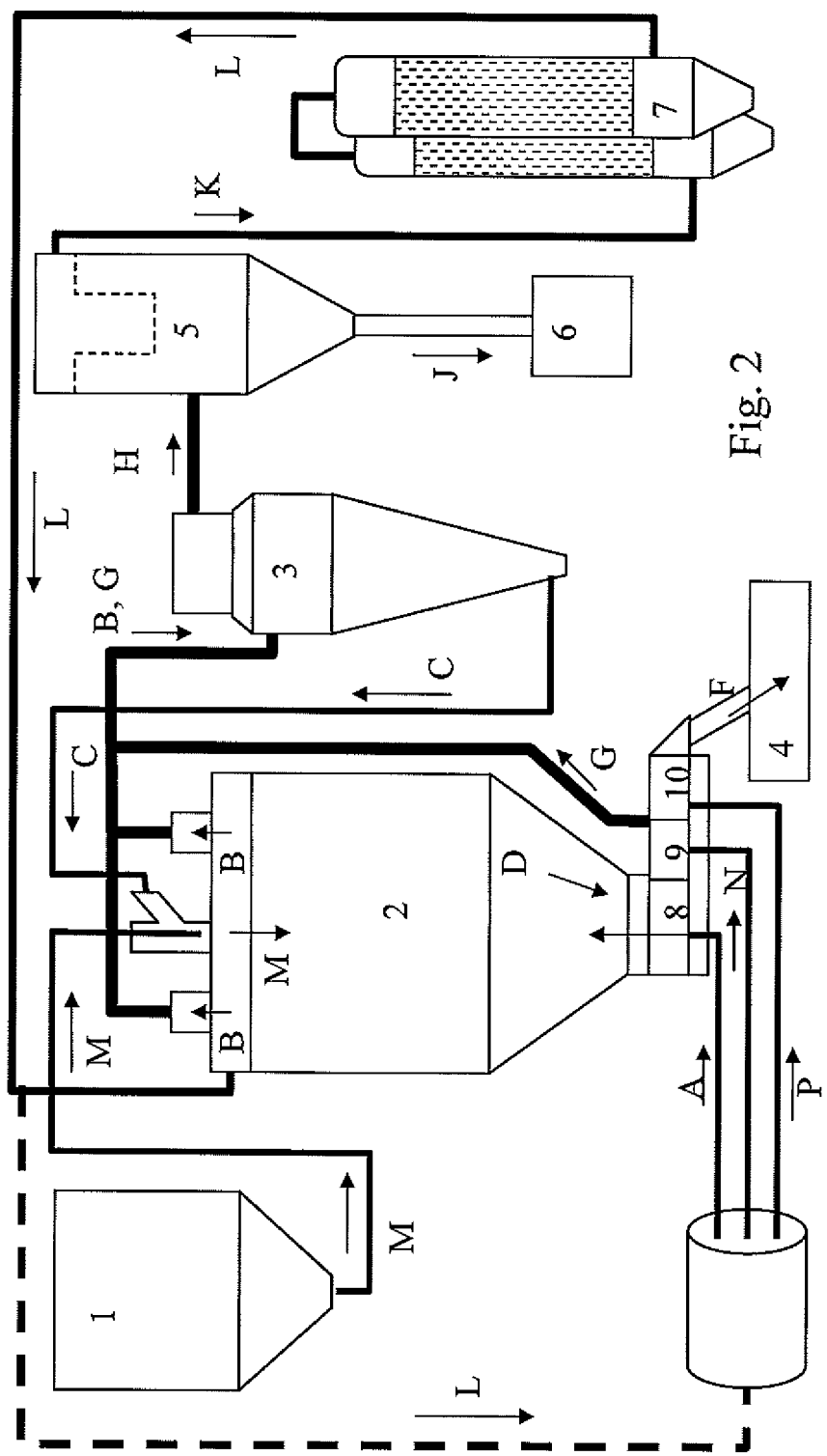
FIG. 2 depicts the general layout of an exemplary fluidized bed spray dryer.

FIG. 2 depicts an exemplary fluidized bed spray dryer system that can be used to prepare a SAE-CD composition of the invention. This system includes a liquid feed tank (1), cylindrical fluidized bed spray drying unit (2), cyclone particle classifier (3), finished-product collection container (4), gas filtration unit (5), waste-product collection container (6), condensers (7), and fluidized bed chambers (8-10). The system can be operated as follows. To begin the process, an aqueous liquid feed containing SAE-CD raw material is transferred from the tank (1) to the dryer (2) via conduit (M). The liquid feed is atomized into the drying chamber in a counter-current manner against the hot gas stream (A) to form an initial fluidized bed of particles. The fine particles formed exit the drying chamber and are conducted via conduit (B) to the cyclone (3), which classifies the particles and returns appropriately-sized fine particles via conduit (C) back into the upper portion of the drying chamber at a location adjacent to and in a co-current fashion with the liquid feed. As additional liquid feed is atomized into the drying chamber larger particles and fine particles are formed, and the larger particles (those not considered "fine" particles) form the fluidized bed in chamber (8). When the particles reach the intended mean particle diameter size, they are conducted to chamber (9), and subsequently, chamber (10). Each chamber includes its own gas inlet and contains a fluidized bed of particles. The gas inlet for chamber (8) is the main hot gas stream (A) that fluidizes the bed of particles in the drying chamber (8). The gas stream (N) for chamber (9) is lower in temperature than the stream (A), and the stream (P) is even lower in temperature. As the particles move from chamber (8) to chamber (9) and then chamber (10), they are cooled. The finished SAE-CD composition is collected from chamber (10) and conducted to the container (4) via a conduit (F). Fine particles present in chambers (9) and (10) are conducted via conduit (G) to the cyclone (3). Gas exiting the cyclone is conducted via conduit (H) into the filter unit (5) to collect any particles not otherwise recycled by the cyclone to the drying chamber. Particles collected in the filter unit are loaded into a collection container (6) for possible reprocessing. Gas exits the filter unit and is conducted through the condenser(s) (7), which remove moisture from the gas. Finally, the gas is either vented or returned back to the drying chamber via conduit (L) and/or the gas streams (A, N, or P).

Figure 3:
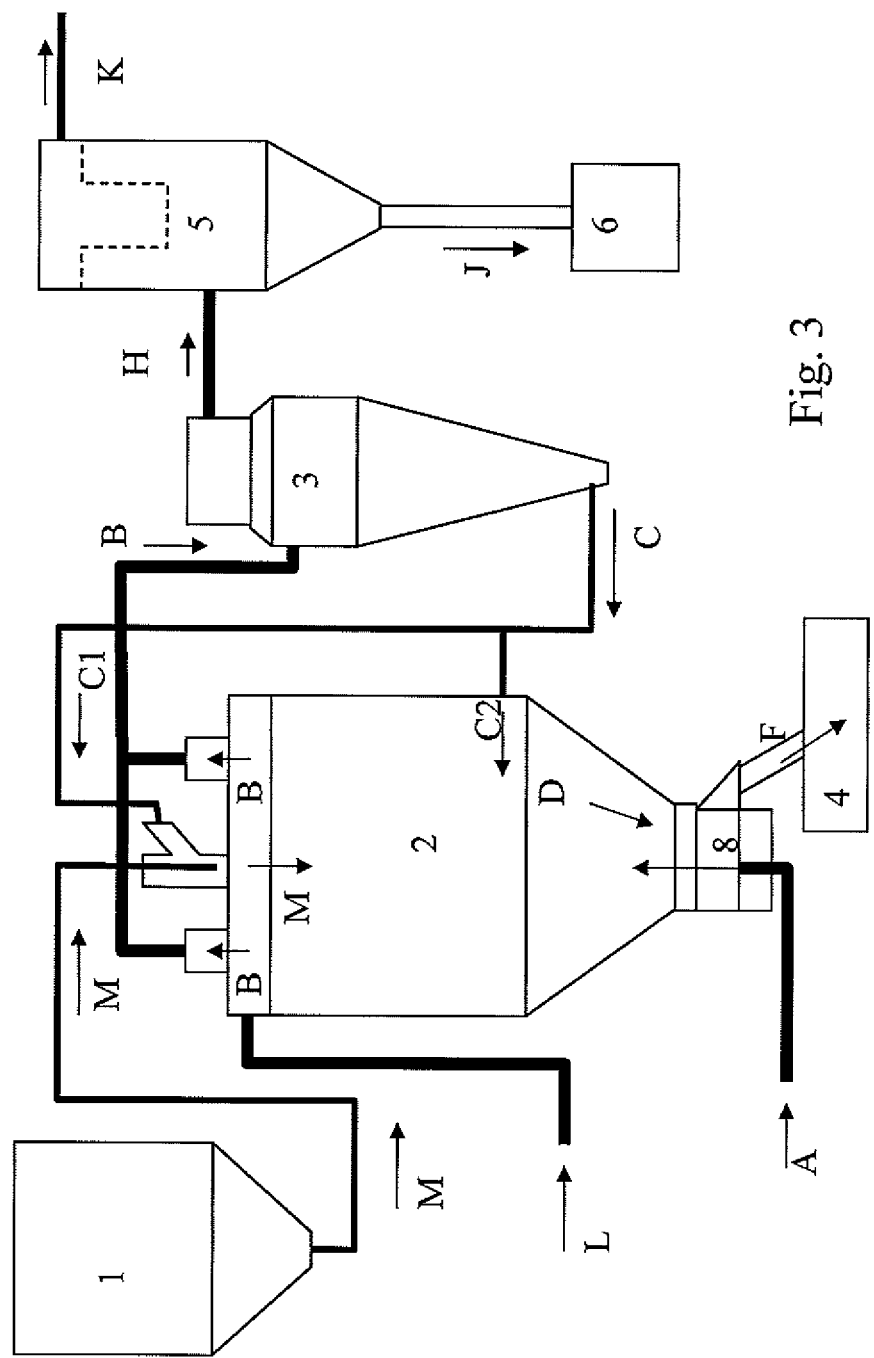
FIG. 3 depicts the general layout of another exemplary fluidized bed spray dryer.

FIG. 3 depicts another exemplary fluidized bed spray dryer system that can be used to prepare a SAE-CD composition of the invention. This system is similar to that of FIG. 2; however, it excludes the chambers (9-10), the particle-recycle conduit (G), and the condenser(s) (7). Moreover, the cyclone returns the fine particles to the drying chamber via conduit (C) and subsequently conduit (C1) and/or conduit (C2). When the fines are introduced into the drying chamber via the conduit (C1), they are introduced in a co-current manner with the flow of liquid feed being atomized into the drying chamber. When the fines are introduced into the drying chamber via the conduit (C2), the fines are introduced in a direction that is tangential to or perpendicular to the flow of gas stream (A) being introduced into the drying chamber and/or the gas inlet (L). Note that this exemplary system does not return gas from the filtration unit back into the drying chamber; however, it can be modified to do so.

Most particles in such fluidized bed chambers typically do not reach the height of the cloud of atomized liquid feed. However, fine particles formed during the process that are recycled back into the drying chamber can be introduced at a location adjacent the liquid feed atomizer or at a location between the atomizer and the fluidized bed.

During operation of either system, the flow of gas stream can be adjusted at various locations within the system in order to modify bed fluidization, drying rate, fines classification, and/or feed rate of the fines into the drying chamber. Fluidized bed spray drying process includes:

providing a liquid feed (solution, suspension or slurry) comprising a liquid carrier and optionally SAE-CD;

providing in a drying chamber a fluidized bed of SAE-CD particles having a first mean particle diameter size, wherein the bed is fluidized with a stream of hot gas flowing in a first direction;

atomizing the liquid feed onto the fluidized bed in the drying chamber to form a particulate SAE-CD composition comprising agglomerated particles having a greater second mean particle diameter size, wherein the atomization is conducted in a second direction and a majority of the liquid carrier has been removed from the particulate composition; and collecting the particulate composition to form the SAE-CD composition.

Specific embodiments of the processes include those wherein: 1) the process further comprises recycling a portion of the smaller particles in the particulate composition back to the drying chamber; 2) the recycled portion of particles is introduced into the drying chamber at a location adjacent the point of introduction of the liquid feed; 3) the recycled portion of particles is introduced into the drying chamber in a direction tangential or perpendicular to the direction of introduction of the liquid feed into the drying chamber; 4) the recycled portion of particles is introduced into the drying chamber at a location adjacent the cone of the drying chamber; 5) the process is conducted in a co-current manner; 6) the process is conducted in a counter-current manner; 7) the process is conducted in a mixed flow manner; 8) the particulate composition comprises less than 18% by wt. of liquid carrier; 9) the liquid carrier is aqueous; 10) the liquid feed comprises SAE-CD; 11) the SAE-CD composition possesses a combination of physical properties as described herein; and 12) the fluidized bed spray dryer has a cylindrical and/or conical drying chamber.

In a co-current fluidized bed spray drying process, the direction of flow of the atomized liquid feed in the drying chamber is the same as the direction of flow of the hot air used to fluidize the bed of particles. The atomizer can be a spray nozzle or a rotary atomizer (e.g. rotating disk). The air current can be controlled such that laminar or turbulent flow occurs predominantly.

In a counter-current fluidized bed spray drying process, the hot air used to fluidize the bed moves through the drying chamber in a direction opposite that of the atomized liquid feed.

In a mixed flow fluidized bed spray drying process, particles move through the drying chamber in both co-current and counter-current phases. This mode requires the use of a nozzle atomizer spraying upwards into an incoming airflow or an atomizer spraying droplets downwards towards an integrated fluid bed, wherein the air inlet and outlet are located at the top of the drying chamber. Additional air inlets will direct flow upwards to fluidize the bed of particles.

The fine or small particles used to form the fluidized bed in the drying chamber can be prepared separately such as by spray drying, milling, grinding, otherwise attritting, sieving, or other suitable means. Otherwise, the fine particles can be prepared in situ by operating the equipment as a conventional spray dryer and subsequently operating the equipment as a fluidized bed spray dryer. In one embodiment, the fine or small particles are obtained by separating those particles from the material removed from the drying chamber and recycling the fine or small particles back into the drying chamber. The invention includes processes whereby the fine particles are introduced into the drying chamber and/or are generated in situ by virtue of drying of the atomized liquid feed.

The process of the invention can be run in a continuous or semicontinuous manner whereby liquid feed containing SAE-CD raw material is introduced into the drying chamber continuously or semicontinuously and SAE-CD composition is removed from the fluidized bed continuously or semicontinuously.

The aqueous liquid carrier used in the liquid feed, which can be a solution or slurry, may or may not contain another material, such as by-product(s) of the sulfoalkylation reaction and subsequent basification of the reaction milieu. As used herein, a liquid carrier is any aqueous medium used in the pharmaceutical sciences used to agglomerate or granulate solids.

The SAE-CD solids content of the liquid feed can range from 0.1 to 80% by wt., 10 to 70% by wt., 30 to 70% by wt., or 40 to 60% by wt. solids. Some embodiments of the liquid feed comprise: 1) only sulfoalkyl ether cyclodextrin and water; or 2) only sulfoalkyl ether cyclodextrin, water and by-products of the synthetic process used to prepare the sulfoalkyl ether cyclodextrin. The sulfoalkyl ether cyclodextrin used in the liquid feed is sometimes referred to herein as the sulfoalkyl ether cyclodextrin raw material.

The liquid feed can be cooled or heated prior to entry into the drying chamber. Temperature can be used to control viscosity of the liquid feed: the higher the temperature, the lower the viscosity. The temperature of the liquid feed can be 0° C. to 100° C., or ambient temperature to 70° C.

The gas used to conduct particles throughout the system is generally a gas such as air, helium, or nitrogen. The system can include a gas-charging unit to load gas for operation, purging and supplementation.

The temperature of the inlet gas can be used to control drying rate of the particles, production rate, extent of agglomeration, water content of the SAE-CD composition and/or type of agglomeration. The temperature can vary from about 100° to about 300° C., about 130° to about 180° C., about 150° to about 170° C., or about 210° to about 250° C.

The SAE-CD composition has a gravitational-flow minimum orifice diameter ranging from about 3-7 mm or 4-6 mm, or less than about 10 mm or less than about 20 mm. The term "gravitational-flow minimum orifice diameter" means the minimum diameter of an orifice through which the SAE-CD composition will provide an acceptable bulk flow. The example below further defines the term. This parameter is determined according to the method of Example 5 wherein a FLOWDEX (Hanson Research Corp., Northridge, Calif.) apparatus is used. The present inventors have succeeded in preparing a SAE-CD composition that has a substantially different minimum orifice diameter than has been prepared by conventional spray drying.

The SAE-CD composition has a CARR's index of less than or about 24% compressibility or less than or about 18% compressibility or less than or about 16% compressibility. As used in this regards, "compressibility" refers to the relative percent reduction that a particulate mass will undergo during the tapped density determination. The CARR's index is a measure of the compressibility of a SAE-CD composition. It is based upon the bulk and tapped density of the material. The CARR's index has been determined according to Example 8 below. The present inventors have succeeded in preparing a spray agglomerated SAE-CD composition having a CARR's index substantially different to other SAE-CD compositions prepared by spray drying, freeze-drying, or spray agglomeration.

The SAE-CD has a true density in the range of about 1.25 to 1.35 g/cm$^3$ or 1.1 to 1.5 g/cm$^3$ or 1.29 to 1.32 g/cm$^3$. True density has been determined according to Example 8 below. The SAE-CD composition of the invention has a substantially different true density than a SAE-CD composition prepared by spray drying.

The SAE-CD composition has a bulk density of about 0.55 to 0.66 g/cm$^3$, about 0.38 to less than 0.55 g/cm$^3$, or about 0.38 to about 0.66 g/cm$^3$. The SAE-CD composition made according to the spray agglomeration process of the invention has a higher bulk density than that of a SAE-CD composition made by another spray dry agglomeration process.

The SAE-CD composition has a tapped density (tap density) of about 0.66 to 0.75 g/cm$^3$, or about 0.49 to 0.66 g/cm$^3$ or about 0.49 to about 0.75 g/cm$^3$ when performed according to USP <616> Method 1. The SAE-CD composition made according to the spray agglomeration process of the invention has a higher tap density than that of a SAE-CD composition made by another spray dry agglomeration process.

Figure 4:
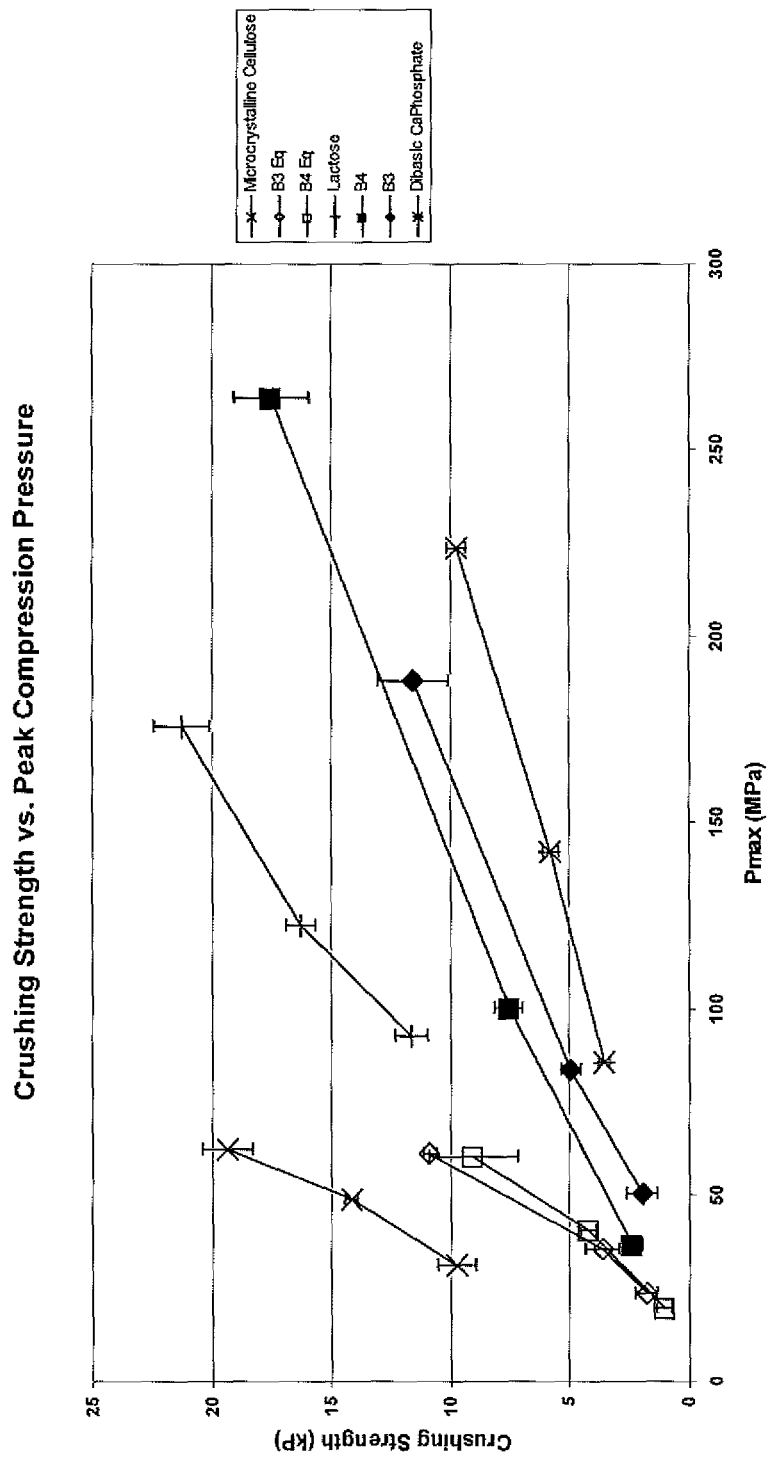
FIG. 4 is a graph depicting the relationship between crushing strength and compression pressure for SAE-CD compositions of the invention containing differing amounts of moisture.

Since solid SAE-CD composition can be used for the manufacture of tablets, especially compressed tablets, its compression crushing strength at different peak compression pressures was determined with SAE-CD compositions having different moisture contents. The method of Example 7 was used to determine this relationship. SAE-CD composition performance was compared (FIG. 4) to that of Avicel PH-200, lactose and Dical, which are three excipients commonly used in the manufacture of tablet formulations. The SAE-CD composition of the invention is highly advantageous, as its compression behavior can be improved by changing its moisture content, particle size and/or particle shape.

Tablet Hardness or Tablet Crushing Strength in units of kiloponds (kP) versus Peak Compression Pressure (Pmax) in units of megapascals (MPa) is presented for SAE-CD composition (SBE7-β-CD) sample (B3, B4) of this invention used 'as is', i.e. as obtained from the fluidized bed spray drying process, and equilibrated (B3 Eq and B4 Eq) over saturated magnesium nitrate. The performance of those samples was compared to that of commercial direct compression bulk excipients, e.g. microcrystalline cellulose or MCC (Avicel PH 200, FMC), lactose monohydrate (SuperTab, The Lactose Co. of New Zealand), dibasic calcium phosphate dihydrate (Emcompress, Penwest Pharm Co.). For the tooling used in this study, 100 MPa is approximately equivalent to 6 kN of force. The 'as is' water content of the SAE-CD composition of this invention was 2.77% and 2.36% for B3 and B4, respectively, as determined by Loss on Drying (LOD) at 110 C via Computrac Model 2000XL (Arizona Instruments, Tempe, Ariz.). The water content after equilibration as determined by LOD was 5.46% and 5.50% for B3 Eq and B4 Eq, respectively.

At lower levels of moisture content, e.g. in the range of about 2 to about 3% by wt. (as determined by LOD run at 104° to 110° C.), the SAE-CD composition had a compression crushing strength in the range of about 1 to about 20 kP (kiloponds) when compressed into a tablet using a Pmax (peak compression pressure) in the range of about 30 to about 275 MPa (megapascals). At higher levels of moisture content, e.g. in the range of about 5 to about 6% by wt. (as determined by LOD), the SAE-CD composition had a compression crushing strength in the range of about 0.5 to about 11 kP when compressed into a tablet using a Pmax in the range of about 15 to about 70 MPa. The mean particle diameter, particle diameter size distribution, and morphology of the SAE-CD composition are readily modified to match the wide variety of micronized drug characteristics that are presented to a formulator of the art. An advantage of the present invention is the ability of an artisan to modulate the physicochemical properties of the SAE-CD composition to match or complement formulation or manufacturing processes, drug properties or excipient properties thereby resulting in an optimal product.

The dosage form of the invention can be used to administer a wide range of active agents. Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, minerals, dietary supplements, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications.

The active agent can be independently selected at each occurrence from pharmaceutical active agents such as an antibiotic agent, antihistamine agent, decongestant, anti-inflammatory agent, antiparasitic agent, antiviral agent, local anesthetic, antifungal agent, antibacterial agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, anti-Parkinson's disease agent, anti-Alzheimer's disease agent, muscle relaxant agent, antimalarial agent, hormonal agent, contraceptive agent, sympathomimetic agent, hypoglycemic agent, anti-hyperglyceridemia agent, anti-dyslipidemia agent, cholesterol reducing agent, bile acid absorption inhibitor, antilipemic agent, ophthalmic agent, electrolytic agent, diagnostic agent, prokinetic agent, gastric acid secretion inhibitor agent, anti-ulcerant agent, anti-flatulent agent, anti-incontinence agent, cardiovascular agent, corticosteroid, $B_2$ adrenoreceptor agonist, dopamine $D_2$ receptor agonist, anticholinergic agent, IL-5 inhibitor, antisense modulators of IL-5, milrinone lactate, tryptase inhibitor, tachykinin receptor antagonist, leukotriene receptor antagonist, 5-lypoxygenase inhibitor, anti-IgE antibody, protease inhibitor or a combination thereof.

Other specific active agents that can be employed according to the invention include pentamidine isethiouate, albuterol sulfate, metaproterenol sulfate, flunisolide, cromolyn sodium, sodium cromoglycate, ergotamine tartrate, levalbuterol, terbutaline, reproterol, salbutamol, salmeterol, formoterol, fenoterol, clenbuterol, bambuterol, tulobuterol, broxaterol, epinephrine, isoprenaline or hexoprenaline, an anticholinergic, such as tiotropium, ipratropium, oxitropium or glycopyrronium; a leukotriene antagonist, such as andolast, iralukast, pranlukast, imitrodast, seratrodast, zileuton, zafirlukast or montelukast; a phosphodiesterase inhibitor, such as filaminast or piclamilast; a paf inhibitor, such as apafant, forapafant or israpafant; a potassium channel opener, such as amiloride or furosemide; a painkiller, such as morphine, fentanyl, pentazocine, buprenorphine, pethidine, tilidine, methadone or heroin; a potency agent, such as sildenafil, alprostadil or phentolamine; a peptide or protein, such as insulin, erythropoietin, gonadotropin or vasopressin; calcitonin, factor ix, granulocyte colony stimulating factor, granulocyte macrophage colony, growth hormone, heparin, heparin (low molecular weight), interferon alpha, interferon beta, interferon gamma, interleukin-2, luteinizing hormone releasing hormone, somatostatin analog, amylin, ciliary neurotrophic factor, growth hormone releasing factor, insulin-like growth factor, insulinotropin, interleukin-1 receptor antagonist, interleukin-3, interleukin-4, interleukin-6, macrophage colony stimulating, factor (m-csf), nerve growth factor, parathyroid hormone, thymosin alpha 1, iib/iiia inhibitor, alpha-1 antitrypsin, anti-rsv antibody, cystic fibrosis transmembrane regulator (cftr) gene, deoxyribonuclease (dnase), bactericidal/permeability (ards), increasing protein anti-cmv antibody, interleukin-1 receptor, or a pharmaceutically acceptable derivative or salt of these compounds.

The active agents (drugs) listed herein should not be considered exhaustive and is merely exemplary of the many embodiments considered within the scope of the invention. Many other active agents can be administered with the composition of the present invention. Suitable drugs are selected from the list of drugs included herein as well as from any other drugs accepted by the U.S.F.D.A. or other similarly recognized authority in Canada (Health Canada), Mexico (Mexico Department of Health), Europe (European Medicines Agency (EMEA)), South America (in particular in Argentina (Administracion Nacional de Medicamentos, Alimentos y Tecnología Médica (ANMAT) and Brazil (Ministério da Saúde)), Australia (Department of Health and Ageing), Africa (in particular in South Africa (Department of Health) and Zimbawe (Ministry of Health and Child Welfare),) or Asia (in particular Japan (Ministry of Health, Labour and Welfare), Taiwan (Executive Yuans Department of Health), and China (Ministry of Health People's Republic of China)) as being suitable for administration to humans or animals. Some embodiments of the invention include those wherein the active substance is pharmacologically or biologically active or wherein the environment of use is the GI tract of a mammal The active agent can be present in its neutral, ionic, salt, basic, acidic, natural, synthetic, diastereomeric, epimeric, isomeric, enantiomerically pure, racemic, solvate, hydrate, anhydrous, chelate, derivative, analog, esterified, non-esterified, or other common form. Whenever an active agent is named herein, all such forms available are included.

An active agent contained within the present formulation can be present as its pharmaceutically acceptable salt or salt-free form. As used herein, "pharmaceutically acceptable salt" refers to derivatives of the disclosed compounds wherein the active agent is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others are known to those of ordinary skill in the art. The pharmaceutically acceptable salts of the present invention can be synthesized from the parent active agent which contains a basic or acidic moiety by conventional chemical methods. Lists of other suitable salts are found in *Remington's Pharmaceutical Sciences*, 17$^{th}$. ed., Mack Publishing Company, Easton, Pa., 1985, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep and humans.

A formulation of the invention can comprise an active agent present in an effective amount. By the term "effective amount", is meant the amount or quantity of active agent that is sufficient to elicit the required or desired response, or in other words, the amount that is sufficient to elicit an appreciable biological response when administered to a subject.

The formulation of the invention can be used to deliver one or more different active agents. Particular combinations of active agents can be provided by the present formulation. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

When combinations of active agents are used, one or both of the active agents can be present in a sub-therapeutic amount. As used herein, a sub-therapeutic amount is that amount of first drug that provides less than a normal therapeutic response in patient to which the first drug is administered in the absence of the second drug of the combination.

In other words, the first and second drugs may together provide an enhanced, improved, additive or synergistic therapeutic benefit as compared to the administration of each drug alone, i.e., in the absence of the other drug.

Following its preparation, the SAE-CD composition can be included in any known pharmaceutical formulation or dosage form. The compositions and formulations of the invention are suitable for administration to a subject by any means employed in the pharmaceutical industry. Exemplary modes of administration include, without limitation, endobronchial (intrapulmonary, intratracheal, intraaveolar), oral, peroral, ocular, ophthalmic, otic, sublingual, buccal, transdermal, transmucosal, rectal, vaginal, uterine, urethral, intrathecal, nasal, parenteral, intraperitoneal, intramuscular, and subdermal administration.

A dosage form is available in a single or multiple dose form containing among other things a quantity of active ingredient and the SAE-CD composition, said quantity being such that one or more predetermined units of the dosage form are normally required for a single therapeutic administration. In the case of multiple dose forms, such as a scored tablet, said predetermined unit will be one fraction such as a half or quarter of the multiple dose form. It will be understood that the specific dose level for any patient will depend upon a variety of factors including the indication being treated, active agent employed, the activity of active agent, severity of the indication, patient health, age, sex, weight, diet, and pharmacological response, the specific dosage form employed and other such factors.

Following preparation of the SAE-CD composition, it can be used to prepare a formulation wherein the SAE-CD composition is complexed with or not complexed with an active agent. By "complexed" is meant "being part of a clathrate or inclusion complex with", i.e., a complexed active agent is part of a clathrate or inclusion complex with a cyclodextrin derivative.

By active agent/CD complex is generally meant a clathrate or inclusion complex of a cyclodextrin derivative and an active agent. The ratio of active agent: CD present in the molecular complex can vary and can be in the range of about 10 to about 0.1, on a molar basis. Thus, the CD will generally be, but need not be, present in excess of the active agent. The amount of excess will be determined by the intrinsic solubility of the agent, the expected dose of the agent, and the binding constant for inclusion complexation between the specific drug (agent) and the specific CD derivative used. It should be noted that the cyclodextrin derivative can be present in uncomplexed form and therefore in amounts substantially in excess of the amount of active agent present. The weight ratio or molar ratio of derivatized cyclodextrin to active agent can exceed 100, 1000 or even more.

Under some conditions, the SAE-CD composition can form one or more ionic bonds with a positively charged acid-ionizable compound. Therefore, it is possible for a compound to be complexed by way of an inclusion complex with the derivatized cyclodextrin and to be non-covalently but ionically bound to the derivatized cyclodextrin.

Even though the SAE-CD composition can be the sole carrier or excipient in a formulation, it is possible to add other carriers to the formulation to further improve its performance.

The SAE-CD composition can be included in any formulation requiring a derivatized cyclodextrin. An active agent included in the formulation can be delivered according to a rapid, immediate, pulsatile, timed, targeted, delayed and/or extended release formulation.

By "immediate release" is meant a release of an active agent to an environment over a period of seconds to no more than about 30 minutes once release has begun and release begins within no more than about 2 minutes after administration. An immediate release does not exhibit a significant delay in the release of drug.

By "rapid release" is meant a release of an active agent to an environment over a period of 1-59 minutes or 0.1 minute to three hours once release has begun and release can begin within a few minutes after administration or after expiration of a delay period (lag time) after administration.

An extended release formulation containing the SAE-CD composition will release drug in an extended manner. Mechanisms employed for such delivery can include active agent release that is pH-dependent or pH-independent; diffusion or dissolution controlled; pseudo-zero order (approximates zero-order release), zero-order, pseudo-first order (approximates first-order release), or first-order; or rapid, slow, delayed, timed or sustained release or otherwise controlled release. The release profile for the active agent can also be sigmoidal in shape, wherein the release profile comprises an initial slow release rate, followed by a middle faster release rate and a final slow release rate of active agent. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "controlled release", "prolonged release", "sustained release", or "slow release", as these terms are used in the pharmaceutical sciences. A controlled release can begin within a few minutes after administration or after expiration of a delay period (lag time) after administration. An extended release can begin within a few minutes after administration or after expiration of a delay period (lag time) after administration.

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. A controlled release can begin within a few minutes after administration or after expiration of a delay period (lag time) after administration.

A timed release dosage form is one that begins to release drug after a predetermined period of time as measured from the moment of initial exposure to the environment of use.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

A targeted release dosage form generally refers to an oral dosage form that designed to deliver drug to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can delivery to other sections of the gastrointestinal tract such as the stomach, jejunum, ileum, duodenum, cecum, large intestine, small intestine, colon, or rectum.

A pulsatile release dosage form is one that provides pulses of high active ingredient concentration, interspersed with low concentration troughs. A pulsatile profile containing two peaks may be described as "bimodal".

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

Extended release formulations can be made according to the procedures described herein or in Biorelated Polymers and Gels: Controlled Release and Applications in Biomedical Engineering (ed. Teruo Okano; 1998); Encyclopedia of Controlled Drug Delivery (ed. Edith Mathiowitz; 1999); Future Strategies for Drug Delivery with Particulate Systems (ed. J. E. Diederichs; 1998); Controlled Release Series (ed. J. M. Anderson; 1987); Controlled Drug Delivery Series (Ed. S. D. Bruck; 1983); Controlled Release of Drugs Series (ed. M. Rosoff; 1989); Controlled Release Technology: Pharmaceutical Applications (ACS Symposium Series No. 348) (eds. P. I. Lee and W. R. Good; 1987); Extended Release Dosage Forms (ed. L. Krowczynski; 1987); Handbook of Pharmaceutical Controlled Release Technology (ed. D. L. Wise; 2000); Intelligent Materials for Controlled Release (ed. S. M. Dinh; 1999); Multicomponent Transport in Polymer Systems for Controlled Release (Polymer Science and Engineering Monograph Series) (ed. A. Polishchuk; 1997); Pharmaceutical Technology: Controlled Drug Release (ed. M. Rubenstein; 1987); Polymers for Controlled Drug Delivery (ed. P. J. Tarcha; 1991); Tailored Polymeric Materials for Controlled Delivery Systems (ACS Symposium Series No. 709) (ed. I. McCulloch; 1998); Oral Colon-Specific Drug Delivery (ed. D. R. Friend, 1992); and other publications known to those of ordinary skill in the art, the entire disclosures of which are hereby incorporated by reference.

The extended release layer can be a matrix diffusion, erosion, dissolution, or disintegration-controlled composition comprising a drug and one or more release rate modifying excipients and other optional excipients.

By "delayed release" is meant that initial release of drug from a respective drug-containing layer occurs after expiration of an approximate delay (or lag) period. For example, if release of drug from the extended release layer is delayed two hours, then release of drug from that layer begins at about two hours after administration of the multi-layered tablet to a subject. In general, a delayed release is opposite an immediate release, wherein release of drug begins after no more than a few minutes after administration. Accordingly, the drug release profile from a particular layer can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

Although not necessary, a formulation of the present invention can include antioxidants, acidifying agents, alkalizing agents, buffering agents, solubility-enhancing agents, penetration enhancers, electrolytes, fragrances, glucoses, glidants, stabilizers, bulking agents, cryoprotectants, plasticizers, flavors, sweeteners, surface tension modifiers, density modifiers, volatility modifiers, hydrophilic polymers, preservatives, antibacterial agents, colorants, antifungal agents, complexation enhancing agents, solvents, salt, water, tonicity modifiers, antifoaming agents, oil, penetration enhancers, other excipients known by those of ordinary skill in the art for use in pharmaceutical formulations, or a combination thereof. Upon each occurrence, these materials can be independently included in the active agent-containing particles or the carrier particles. For example, the carrier might include one or more of these materials and the active agent-containing particles might also include one or more of these materials.

As used herein, the term "glidant" is intended to mean an agent used to promote flowability of the dry powder. Such compounds include, by way of example and without limitation, magnesium stearate, sodium dodecylsulfate, colloidal silica, cornstarch, talc, calcium silicate, magnesium silicate, colloidal silicon, silicon hydrogel and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "alkalizing agent" is intended to mean a compound used to provide alkaline medium when the dry powder of the invention is exposed to water. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium when the dry powder of the invention is exposed to water. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "buffering agent" is intended to mean a compound used to resist change in pH upon exposure to a medium of a different pH. Buffers are used in the present compositions to adjust the pH to a range of between about 2 and about 8, about 3 to about 7, or about 4 to about 5. By controlling the pH of the dry powder, irritation to the respiratory tract can be minimized. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art. Other buffers include citric acid/phosphate mixture, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis 2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), TRIZMA™ (tris(hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)-methylglycine), GLY-GLY (glycylglycine), BICINE (N,N-bis(2-hydroxyethyl) glycine), HEPBS (N-(2-hydroxyethyl)piperazine-N'-(4-butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art.

A complexation-enhancing agent is a compound, or compounds, that enhance(s) the complexation of an active agent with the derivatized cyclodextrin. When the complexation-enhancing agent is present, the required ratio of derivatized cyclodextrin to active agent may need to be changed such that less derivatized cyclodextrin is required. Suitable complexation enhancing agents include one or more pharmacologically inert water soluble polymers, hydroxy acids, and other organic compounds typically used in liquid formulations to enhance the complexation of a particular agent with cyclodextrins. Suitable water soluble polymers include water soluble natural polymers, water soluble semisynthetic polymers (such as the water soluble derivatives of cellulose) and water soluble synthetic polymers. The natural polymers include polysaccharides such as inulin, pectins, align derivatives and agar, and polypeptides such as casein and gelatin. The semi-synthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose, hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Suitable hydroxy acids include by way of example, and without limitation, citric acid, malic acid, lactic acid, and tartaric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and iron oxide (black, red, yellow), other F.D. & C. dyes and natural coloring agents such as grape skin extract, beet red powder, beta-carotene, annato, carmine, turmeric, paprika, combinations thereof and other such materials known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, simethicone, octoxynol and others known to those of ordinary skill in the art.

Hydrophilic polymers can be used to improve the performance of formulations containing a cyclodextrin. Loftsson (U.S. Pat. No. 5,324,718 and No. 5,472,954) has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; *Pharmazie,* 53(11), 733-740 (1998); *Pharm. Technol. Eur.,* 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Tones; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, Aug. 23-27 (1998), CELL-016, American Chemical Society; *Journal of Controlled Release,* (1997), 44/1 (95-99); *Pharm. Res.* (1997) 14(11), S203; *Investigative Ophthalmology & Visual Science,* (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, Mar. 31-Apr. 2, (1996), 373-376. (Editor(s): Szejtli, J.; Szente, L. Kluwer: Dordrecht, Neth.); *Pharmaceutical Sciences* (1996), 2(6), 277-279; *European Journal of Pharmaceutical Sciences,* (1996) 4(SUPPL.), 5144; Third European Congress of Pharmaceutical Sciences Edinburgh, Scotland, UK Sep. 15-17, 1996; *Pharmazie,* (1996), 51(1), 39-42; *Eur. J. Pharm. Sci.* (1996), 4(Suppl.), 5143; U.S. Pat. No. 5,472,954 and No. 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences,* (1994) 2, 297-301; *Pharmaceutical Research* (New York), (1994) 11(10), 5225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences, 18th Edition*, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences,* 3rd edition (Lea & Febinger, Philadelphia, Pa., 1983, pp. 592-638); A. T. Florence and D. Altwood, (*Physicochemical Principles of Pharmacy, 2nd Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, align derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

A solubility-enhancing agent can be added to a formulation of the invention. A solubility-enhancing agent is a compound, or compounds, that enhance(s) the solubility of active agent in an aqueous or moist environment, such as the lining of respiratory tract. Suitable solubility enhancing agents include one or more organic solvents, detergents, soaps, surfactants and other organic compounds typically used in parenteral formulations to enhance the solubility of a particular agent. Suitable organic solvents include, for example, ethanol, glycerin, poly (ethylene glycols), propylene glycol, poly(propylene glycols), poloxamers, and others known to those of ordinary skill in the art.

As used herein, the term "cryoprotectant" is intended to mean a compound used to protect an active agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

Plasticizers can also be included in the preparations of the invention to modify the properties and characteristics thereof. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in a formulation of the invention. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

As used herein, the term "flavor" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly flavors are the grape and cherry flavors and citrus flavors such as orange.

As used herein, the term "sweetener" is intended to mean a compound used to impart sweetness to a preparation. Such compounds include, by way of example and without limitation, aspartame, dextrose, glycerin, mannitol, saccharin sodium, sorbitol, fructose, high fructose corn syrup, maltodextrin, sucralose, sucrose, other materials known to one of ordinary skill in the art, and combinations thereof.

As used herein, a penetration enhancer is an agent or combination of agents that enhances penetration of an active agent through tissue. Penetration enhancers which can be included in a formulation of the invention include, by way of example and without limitation, calcium chelators such as EDTA, methylated P-cyclodextrin, and polycarboxylic acids; surfactants such as sodium lauryl sulfate, sodium dodecyl sulfate, carnitine, carnitine esters, and tween; bile salts such as sodium taurocholate; fatty acids such as oleic and linoleic acid; and non-surfactants such as AZONE™ and dialkyl sulfoxides; E-flux inhibitors such as AV171 (AyMax, Inc., South San Francisco, Calif.), D-α-tocopheryl polyethylene glycol 1000 succinate (TPGS), and peppermint oil; chitosan and chitosan derivatives such as N-methyl chitosan, N-trimethyl chitosan, mono-N-carboxymethyl chitosan, quaternized chitosan derivatives; SNAC (N-(8-(2-hydroxybenzoyl)amino) caprylate) and SNAD (N-(10-(2-hydroxybenzoyl)amino)-decanoate) (Emisphere Technologies, Inc., Tarrytown, N.Y.); N-acylated non-alpha amino acids; HEMISPHERE brand delivery agents; Gélucire 44/14 or Vitamin E TPGS; CARBOPOL® 934P; others known to those of ordinary skill in the art; and combinations thereof.

As used herein, a fragrance is a relatively volatile substance or combination of substances that produces a detectable aroma, odor or scent. Exemplary fragrances include those generally accepted as FD&C.

A "surface tension modifier" is a material or combination of materials capable of modifying the surface properties of a composition according to the invention. A surface tension modifier can include a surfactant, detergent or soap. It can be included in the carrier particles, the active agent-containing particles or both.

A "density modifier" is a material or combination of materials that is included in a composition of the invention to increase or decrease the density thereof. It can be included in the carrier particles, the active agent-containing particles or both. A density modifier can be used to increase or decrease (as needed) the density of the carrier in order enhance dispersion of the active agent from the carrier. Likewise, a density modifier can be used to decrease or increase, respectively, (as needed) the density of the active agent containing particles.

A "volatility modifier" is a material or combination of materials added to modify the volatility of an active agent. In one embodiment, the volatility modifier increases the volatility of the active agent. In another, embodiment, the volatility modifier decreases the volatility of the active agent.

As used herein, the term "stabilizer" is intended to mean a compound used to stabilize the therapeutic agent against physical, chemical, or biochemical process that would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "bulking agent" is intended to mean a compound used to add bulk to the lyophilized product and/or assist in the control of the properties of a formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

It should be understood that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

In view of the above description and the examples below, one of ordinary skill in the art will be able to practice the invention as claimed without undue experimentation. The foregoing will be better understood with reference to the following examples that detail certain procedures for the preparation of compositions and formulations according to the present invention. All references made to these examples are for the purposes of illustration. The following examples should not be considered exhaustive, but merely illustrative of only a few of the many embodiments contemplated by the present invention.

EXAMPLE 1

Exemplary Formulations were Made According to the Following General Procedures

Method A. Solid Formulation in Admixture

A solid composition comprising cyclodextrin is mixed with a solid composition comprising active agent until homogeneity. The cyclodextrin-containing and active agent-containing compositions contain less than about 20% wt. water. Mixing of the two compositions can also include simultaneous attritting thereof or attrition can be performed as a separate process step. For example, the cyclodextrin-containing composition and the active agent-containing compositions are each attritted separately prior to mixing. One or more additional excipients can be included in the SAE-CD composition and/or the active agent composition.

Method B. Liquid Formulation

An SAE-CD composition is mixed with a liquid carrier optionally containing an active agent. The SAE-CD composition can be mixed with the liquid carrier either prior to, after or during addition of the active agent, if one is present. One or more other excipients can be included in the formulation. If needed, heat can be applied to promote mixing or dissolution.

EXAMPLE 2

Preparation of SAE-CD Solid Compositions

In Methods A and B below, the SAE-CD starting material was provided in an aqueous liquid carrier, and the SAE-CD starting material was prepared according to a known literature method. Particular embodiments included SAE-CD starting material dissolved in water. The concentration of SAE-CD in the liquid carrier was varied as needed to provide a liquid feed of the desired viscosity or solids content.

Method A. Fluidized Bed Spray Drying

An SAE-CD carrier was prepared by spray agglomeration in an FSD-16 fluid spray drier apparatus (GEA Niro Inc., Columbia Md.) as follows. Several solutions of sulfobutyl ether-beta-cyclodextrin (degree of substitution~7, SBE7-BCD) at 20.1-49.8% solids were agglomerated in the FSD-16 using a top mounted Spraying Systems pressure nozzle at atomization pressures of 1,500-2,000 psig and feed temperature ~25° C. Process conditions were inlet/outlet temperatures of 210-250/83-100° C., fluid bed inlet temperatures of 80-100° C., and fluid product bed temperatures of 67-87° C. Fines return at the atomizer nozzle and at the chamber cone was investigated during separate runs. The drying gas flows are heated electrically.

Feed solutions containing SAE-CD were prepared by adding powdered constituents to the required amount of water under heat and agitation in the feed tank.

Method B. Fluidized Bed Spray Drying

An SAE-CD composition was prepared by spray agglomeration in an FSD-12.5 fluid spray drier apparatus (GEA Niro Inc., Columbia Md.) with attached 3-chamber fluidization bed. The inner fluid bed chamber (chamber 1) was directly open to the drying chamber and was used for final agglomeration, drying of agglomerates and dedusting. The outer ring fluid bed chambers 2 and 3 are connected sequentially to chamber 1 such that product moves from chamber 1 to chamber 2 to chamber 3 as controlled by process conditions. Chamber 2 was used for post drying and continued dedusting. Chamber 3 was used for cooling and final dedusting. The final product was taken from chamber 3. The drying gas ($N_2$) flows are heated electrically and the main drying gas was introduced into the drying chamber through a ceiling air disperser. The drying gas to the three fluid bed chambers was evenly distributed across perforated plates. The drying gas flows were individually adjusted to the different fluid bed chambers.

Solutions of sulfobutyl ether-beta-cyclodextrin (degree of substitution~7, SBE7-BCD) at 48-52% wt solids were agglomerated in the FSD-12.5 using a top-mounted Spraying Systems pressure nozzle at atomization pressures of 10-50 bar and a solution temperature of 45-55° C. Process conditions were inlet/outlet temperatures of 150-170/70-90° C., chamber 1 fluid bed inlet temperatures of 100-150° C., and chamber 1 product bed temperatures of 60-100° C. Fines were returned at a location adjacent the atomizer nozzle.

EXAMPLE 3

The particle diameter (size) distribution of several SAE-CD compositions (sulfobutyl ether-beta-cyclodextrin, degree of substitution~7) was determined by laser diffraction (Malvern Instruments Inc, Model 2000, South Borough, Mass.), equipped with a dry powder feeder attachment. The dispersion pressure versus particle size curve was generated and based upon a dispersion pressure of 60 psi. The powder was sampled using 500 detector sweeps for statistical validity. The obscuration values were monitored to ensure adequate data acquisition. The 300 mm focal length detector lens was used, providing a size range of 5.8 to 564 µ.

The particle size analysis data for exemplary SAE-CD compositions of sulfobutyl ether-beta-cyclodextrin with an average degree of substitution of ~7, SBE7-BCD, is included in the table below. The data for each composition indicate the particle diameters in microns corresponding to the De Brouckere mean diameter (D[4,3]) or the particle size cutoffs for the 10%, 50% or 90% cumulative volume fractions. (µ is taken to mean micron.)

|  | Mean Diameter | Particle Size Cutoff at the Stated Volume Distribution Percentiles | | |
|---|---|---|---|---|
| SAE-CD Lot | (D[4,3]) Size (μ) | 10% D[v, 0.1] | 50% D[v, 0.5] | 90% D[v, 0.9] |
| *B3 | 78.7 | 28.7 | 67.9 | 138.1 |
| B4 | 86.9 | 30.2 | 79.1 | 154.1 |
| B5 | 83.8 | 33.1 | 76.7 | 145.4 |
| B9 | 104.9 | 34.9 | 96.5 | 184.9 |
| **A1 | 175 | | | |
| A2 | 194 | | | |
| A3 | 119 | | | |
| A4 | 125 | | | |
| A5 | 92 | | | |
| A6 | 187 | | | |
| A7 | 164 | | | |

*"B#" denotes a SAE-CD composition made according to Example 2, Method B, wherein "#" indicates the lot number of the sample.
**"A#" denotes a SAE-CD composition made according to Example 2, Method A, wherein "#" indicates the lot number of the sample.

EXAMPLE 4

The moisture content of the SAE-CD compositions was measured via the Karl Fisher method (USP<921>, Method Ia) or the moisture balance method.

Moisture Balance Method

Computrac Model 200 XL moisture balance (Arizona Instruments, Tempe, Ariz.) was used to determine the weight loss of selected powder samples over time as the powder was exposed to infrared heating. The powders were weighed (approximately 1 g for each sample), heated at 110° C. until no change in weight was observed, and the percentage weight loss calculated.

EXAMPLE 5

The flowability of solid SAE-CD compositions was determined with a test apparatus (Flodex™, Hanson Research Corp., Northridge, Calif.) having:
  A stainless steel cylinder with an approximate capacity of 200 mL
  A series of stainless steel disks. Each disk having a precise hole in the center in graduated sizes differing 1-2 mm in diameter that is easily attached to form a bottom for the cylinder.
  A shutter that covers the hole and that may be quickly removed without vibration to allow the powder to flow through the selected hole.
  An adjustable funnel for loading the sample cylinder with a free fall of the test powder.
  A suitable container to collect the powder that flows through the unit.

The funnel was mounted above the cylinder such that the bottom of the funnel was near but not touching the powder surface once loaded into the cylinder. A disk was inserted into the bottom of the cylinder and the hole in the disk was closed. A powder load of 50 g was then poured through the funnel into the middle of the cylinder. The powder was allowed to set in the cylinder for at least 30 seconds, then the hole in the disk was opened quickly and without vibration. The flow through the disk opening was then observed. A positive result was when the powder flowed through the hole leaving a cavity shaped like an upside-down, truncated cone in 3 of 3 trials and the powder that falls involves the entire height of the powder (not less than 60 mm).

A negative result was noted when the powder fell abruptly through the hole forming a cylindrical cavity in the remaining powder.

If the result was positive, the procedure was repeated with disks having smaller diameter holes until the smallest diameter hole still giving a positive result in 3 of 3 trials was determined.

If the result was negative, the procedure was repeated with disks having larger diameter holes until the smallest diameter hole giving a positive result in 3 of 3 trials was determined Results of the measurements for SAE-CD compositions (sulfobutyl ether-beta-cyclodextrin with a degree of substitution of ~7, SBE7-B-CD) are given below.

| SBE7-B-CD lot | Minimum orifice diameter (mm) |
|---|---|
| B4 | 6 |
| B9 | 6 |
| A1 | 9 |
| A2 | 8 |
| A3 | 5 |
| A4 | 4 |
| A5 | 10 |
| A6 | 12 |
| A7 | 10 |

EXAMPLE 6

The average dissolution time of SAE-CD compositions (sulfobutyl ether-beta-cyclodextrin with an average degree of substitution ~7, SBE7-BCD) was determined by a flow-through dissolution device comprising a glass filter holder (Millipore Corp., Billerica, Mass.) attached to a pump and water reservoir. The filter holder was comprised of a ~300 mL capacity funnel and a fritted glass base held together with a metal clamp.

The test was conducted by placing a 2.5 g sample of the powder onto a 47 mm×10 micron pore size filter mounted between the sections of the filter holder. Water at ~25° C. was pumped at a rate of 100 mL per minute through the bottom of the apparatus such that the water would rise through the filter and into the reservoir. The sample was observed to determine the time required for dissolution of all the solids. If the sample floated and required longer than 2.5 minutes to dissolve, the pump was stopped after delivering 250 mL.

Representative data for sulfobutyl lether-beta-cyclodextrin with an average degree of substitution of 7 (SBE$_7$-CD) are included in the table below.

| SBE$_7$-CD Composition | Dissolution Time (minutes) | | |
|---|---|---|---|
| | Run 1 | Run 2 | Average |
| B3 | 3.0 | 3.5 | 3.25 |
| B4 | 2.0 | 2.25 | 2.13 |
| B5 | 2.0 | 2.0 | 2.0 |
| B6 | 2.5 | 2.5 | 2.5 |
| B8 | 2.0 | 2.5 | 2.25 |
| B10 | 2.25 | 2.0 | 2.13 |
| A5 | 2.0 | 2.0 | 2.0 |

EXAMPLE 7

SAE-CD compositions were compared in compaction studies to samples of commercial powders often used in preparing tablets, e.g. microcrystalline cellulose (Avicel 200), lactose USP, and dibasic calcium phosphate dihydrate (Di-Cal).

The powders were compressed on an instrumented Colton single station press, running at 15 tablets per minute. The press had an instrumented upper and lower punch compression force and displacement. The sample weight was 200 mg and the samples were compressed to three different tablet hardnesses of approximately 5, 10 and 15 kP using flat-faced punches with a diameter of 0.345 inches. The force and displacement data were collected using a 4-channel, 12-bit digital oscilloscope (Model #420, Nicolet Instrument Corp., Madison, Wis., USA); samples were collected every msec simultaneously for each of the four channels. The die was lubricated with a 10% (w/v) slurry of magnesium stearate in acetone applied with a cotton swab. To maintain tablet-to-tablet consistency, a standardized procedure was developed for swabbing and drying the slurry onto the die wall. The die-wall coverage was also checked by visual inspection. To reduce signal noise, Fast Fourier transform (FFT) was performed on the upper and lower punch data using Igor Pro version 3.1 (Wavemetrics, Inc., Oregon). The Igor Pro was also used to find the Pmax in the average tablet pressure curve (i.e., maximum punch pressure) after the FFT had been performed; the software algorithm found the minimum using the derivative of the curve.

Tablet breaking strength was measured with a KEY® HT-300 hardness tester (Englishtown, N.J.). A dial indicator was used to measure post compression tablet height. Typically, 5 tablets were compressed and tested for hardness at each of the three target hardness levels.

EXAMPLE 8

The density and compressibility of SAE-CD compositions was determined by the following methods:

Method A. Bulk Density

Bulk density of SAE-CD compositions was determined according to USP <616> Method I, using a 100 mL graduated cylinder.

Method B. Tapped Density

Tapped density of SAE-CD compositions was determined by USP <616> Method I, using a 100 mL graduated cylinder.

Method C. Carr's Compressibility Index

The Carr's compressibility index of SAE-CD compositions was calculated according to the formula:

$$\% \text{ compressibility} = \left( \frac{\text{Tap Density} - \text{Bulk Density}}{\text{Tap Density}} \right) \times 100\%$$

Method D. True Density

The true density of SAE-CD compositions was determined with a Multivolume Pycnometer (Micromeritics Instrument Corp., Model 1305, Norcross, Ga.) according to the USP <699> method. A sample holder having a one cm³ volume was used for all measurements.

The results of the measurements for SAE-CD compositions (sulfobutyl ether-beta-cyclodextrin with and average degree of substitution~7, SBE7-BCD, are given in the table below.

| SBE7-BCD Sample | Bulk Density (g/cm³) | Tapped Density (g/cm³) | Carr's Index (%) | True Density (g/cm³) |
|---|---|---|---|---|
| B3 | 0.610 | 0.731 | 16.6 | 1.29 |
| B4 | 0.594 | 0.701 | 15.3 | 1.30 |
| B5 | 0.601 | 0.708 | 15.1 | 1.30 |
| B6 | 0.604 | 0.692 | 12.8 | |
| B8 | 0.573 | 0.670 | 14.6 | |
| B9 | | | | 1.28 |
| B10 | 0.595 | 0.694 | 14.2 | |
| A1 | 0.429 | 0.564 | 23.9 | |
| A2 | 0.410 | 0.539 | 23.9 | |
| A3 | 0.549 | 0.670 | 18.1 | |
| A4 | 0.549 | 0.661 | 16.9 | |
| A5 | 0.481 | 0.574 | 16.0 | |
| A6 | 0.433 | 0.528 | 18.0 | |
| A7 | 0.381 | 0.495 | 23.0 | |

EXAMPLE 9

A dry powder formulation suitable for administration with a DPI device comprises one or more active agents, SAE-CD composition carrier and optionally one or more excipients selected from the group consisting of an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, or a combination thereof. The SAE-CD carrier comprises about 50%-99.9% wt. of the formulation, and it has a median particle diameter of less than 420 microns. The active agent-containing particles have a median particle diameter between about 0.1 to 10 microns. The carrier has a span of about 1.5 to 2.9, and the carrier has been made according to invention, and optionally attritting the solid to form the particulate carrier. The SAE-CD used in the carrier has an average DS in the range of about 1 to 12.

EXAMPLE 10

A compressed rapid release tablet comprising sulfobutyl ether-beta-cyclodextrin with an average degree of substitution of 4 (SBE$_4$-βCD, SAE-CD composition), and piroxicam is prepared according to the following formula and procedure.

| Ingredient | Amount (mg) |
|---|---|
| 1: Piroxicam | 10 |
| 1: SBE$_4$-βCD | 77 |
| 2: sorbitol | 45 |
| 2: dextrose | 50 |
| 2: citric acid | 10 |
| 2: xylitol | 47.5 |
| 2: PEG 3350 | 9 |
| 3: magnesium stearate | 1.5 |
| 3: fumed silicon dioxide | 1.5 |
| 3: croscarmellose sodium | 5.5 |
| Total | 257 |

The above ingredients are used to make a 257 mg tablet core having a rapid release profile. The numbers beside the ingredients indicates the general order of addition. After each group of ingredients is added, the mixture is dry blended for 5-10 min. The magnesium stearate, fumed silicon dioxide (CABOSIL™ M5P) and croscarmellose sodium are added in separately (step 3) from other ingredients and an additional 5 min dry blend step is added to the general procedure.

The powder is then compressed to form a tablet with a hardness of about 8-10 Kg.

EXAMPLE 11

A controlled release tablet comprising an SAE-CD composition, sulfobutyl ether-beta-cyclodextrin with an average degree of substitution of 7 (SBE$_7$-βCD), and prednisolone is prepared according to the following formula and procedure.

| Ingredient | Amount (mg) |
| --- | --- |
| Prednisolone | 15 |
| SBE$_7$-βCD | 210 |
| Hydroxypropyl methylcellulose (HPMC K100M) | 75 |
| Total | 300 |

The above ingredients are used to make a 300 mg tablet core having a controlled release profile. The ingredients are blended by hand and individual tablets are prepared on a carver press under a pressure of 1 ton for 7 seconds. The tablets are prepared using a 5/16" standard cup concave tooling.

EXAMPLE 12

An orodispersable immediate release tablet comprising an SAE-CD composition, sulfobutyl ether-gamma-cyclodextrin with an average degree of substitution of 7 (SBE$_7$-γCD), and zaleplon is prepared according to the following formula and procedure.

| Ingredient | Amount per tablet (mg) |
| --- | --- |
| Zaleplon | 5 |
| Croscarmellose sodium (Ac-Di-Sol) | 24 |
| SBE$_7$-γCD | 118 |
| Microcrystalline cellulose (Avicel PH102) | 150 |
| Colloidal silicon dioxide (Cab-O-Sil) | 1.5 |
| Magnesium stearate | 1.5 |
| Total | 300 |

All tablet ingredients are sieved through 40-mesh screen (US Standard) prior to weighing, and then all ingredients except magnesium (Mg) stearate are mixed in a glass bottle using a geometric dilution technique. The powder blend is then passed through the 40-mesh screen twice to facilitate homogenous mixing of all ingredients. Prior to mechanical compression, Mg stearate is added and then mixed for an additional minute. Lastly, the final blend is compressed into tablets with 7-mm concave tooling using a rotary tablet press to give a tablet hardness of approximately 3.0 kiloponds (kp).

EXAMPLE 13

A constitutable powdered formulation of lamotrigine and a SAE-CD composition, sulfobutyl ether-beta-cyclodextrin with an average degree of substitution of 7 (SBE$_7$-βCD), was prepared using the following formula.

| Ingredient | Amount (g) |
| --- | --- |
| Lamotrigine | 7.50 |
| SBE$_7$-βCD | 37.5 |
| Citric Acid USP | 3.75 |
| Xylitol | 300 |
| Sodium Saccharin | 0.75 |
| Benzoic acid | 1.28 |
| Strawberry Flavor | 1.4 |
| Xanthan gum | 1.5 |
| Total | 353.68 |

The sodium saccharin, benzoic acid, strawberry flavor, citric acid, and xanthan gum are combined together and mixed well. The lamotrigine is added to the blend with further mixing then the SBE$_7$-βCD is added and mixing is continued. The xylitol is then added to the resulting powder with geometric dilution and further mixing.

The powder can be constituted with water to give a final volume of 750 mL.

The following terms are defined as detailed below.

| TERM | DEFINITION |
| --- | --- |
| Agglomerate | A collection of particles that are fused together and act as a larger particle. |
| Bulk density | Mass of bulk powder divided by the bulk volume |
| Carr's Index | Measure of the bulk flow properties of powders. |
| CD | Cyclodextrin |
| DPI | Dry powder inhaler |
| KF | Karl Fisher Analysis |
| MDI | Metered dose inhaler, or more correctly, propellant driven metered dose inhaler |
| monodisperse | In terms of particle size, refers to a population of particles that have a uniform particle size |
| nC | nanoCoulomb, measure of charge |
| ND | Not determined |
| pMDI | pressurized metered dose inhaler |
| SEM | Scanning electron microscope |
| Tapped density | Mass of bulk powder divided by the volume of packed powder (following compaction of the powder by vertical tapping) |

As used herein, the term "about" means +/−10% of the value indicated.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure. The disclosure of any patent or other publication cited herein is incorporated herein by reference.

The invention claimed is:

1. A composition comprising a sulfoalkyl ether cyclodextrin composition, wherein the sulfoalkyl ether cyclodextrin composition has:
   a. a moisture content below the point of deliquescence of the sulfoalkyl ether cyclodextrin composition;
   b. a bulk density in the range of about 0.55 to about 0.66 g/cm$^3$; and
   c. a tapped density in the range of about 0.66 to about 0.75 g/cm$^3$.

2. The composition of claim 1, wherein the sulfoalkyl ether cyclodextrin composition has a moisture content of less than about 18% by wt.

3. The composition of claim 1, wherein the sulfoalkyl ether cyclodextrin composition has a true density in the range of about 1.1 to 1.5 g/cm$^3$.

4. The composition of claim 1, wherein the sulfoalkyl ether cyclodextrin composition has a CARR's index of less than or about 24%.

5. The composition of claim 1, wherein the sulfoalkyl ether cyclodextrin composition has a gravitational-flow minimum orifice diameter of less than about 20 mm.

6. The composition of claim 1, wherein the sulfoalkyl ether cyclodextrin composition has been prepared by fluidized bed spray drying.

7. The composition of claim 1, wherein the sulfoalkyl ether cyclodextrin composition comprises agglomerated particles.

8. The composition of claim 7, wherein the agglomerated particles have a mean particle diameter less than or equal to 110 microns.

9. The composition of claim 7, wherein the agglomerated particles have a mean particle diameter of 92 to 200 microns.

10. The composition of claim 1, wherein the sulfoalkyl ether cyclodextrin composition has a moisture content in the range of about 2 to about 3% by wt. and a compression crushing strength in the range of about 1.0 to about 20 kP when compressed into a tablet using a Pmax in the range of about 30 to about 275 MPa.

11. The composition of claim 1, wherein the sulfoalkyl ether cyclodextrin composition has a moisture content in the range of about 5-6% by wt. and a compression crushing strength in the range of about 0.5 to 11 kP when compressed into a tablet using a Pmax in the range of about 15-70 MPa.

12. The composition of claim 1, wherein 2.5 g of the sulfoalkyl ether composition has an average dissolution time of less than 4.5 min when placed in water.

13. The composition of claim 1, wherein at least 90% of the particle volume of the sulfoalkyl ether composition is made of particles having calculated diameters greater than or equal to 25 microns.

14. The composition of claim 1, wherein the sulfoalkyl ether cyclodextrin composition further has two or more of the following properties:
   a. a moisture content of less than or equal to 18% by wt.;
   b. a true density in the range of 1.1 to 1.5 g/cm$^3$;
   c. a CARR's index of less than or equal to 24%;
   d. a gravitational-flow minimum orifice diameter of less than 20 mm;
   e. a moisture content in the range of 2-3% by wt. and a compression crushing strength in the range of 1.0 to 20 kP when compressed into a tablet using a Pmax in the range of 50-200 MPa; and
   f. a moisture content in the range of 5-6% by wt. and a compression crushing strength in the range of 0.5 to 11 kP when compressed into a tablet using a Pmax in the range of 15-70 MPa.

15. A process for preparing a particulate sulfoalkyl ether composition, the process comprising:
   a. providing an aqueous liquid feed comprising water and sulfoalkyl ether cyclodextrin; and
   b. subjecting the liquid feed to a combination fluidized bed spray drying process whereby the sulfoalkyl ether cyclodextrin is dried to below the point of deliquescence to form a particulate sulfoalkyl ether cyclodextrin composition comprising agglomerated particles and having a CARR's index of less than or equal to 24%, a bulk density in the range of 0.55 to 0.66 g/cm$^3$, and a tapped density in the range of 0.66 to 0.75 g/cm$^3$.

16. The process of claim 15 wherein the fluidized bed spray drying process comprises:
   providing an aqueous liquid feed comprising a liquid carrier and sulfoalkyl ether cyclodextrin;
   providing in a drying chamber a fluidized bed of sulfoalkyl ether cycodextrin particles having a first mean particle diameter, wherein the bed is fluidized with a stream of heated gas flowing in a first direction;
   atomizing the liquid feed with an atomizer onto particles in the drying chamber to form a particulate sulfoalkyl ether cyclodextrin composition comprising agglomerated particles having a greater second mean particle diameter, wherein the atomization is conducted in a second direction and a majority of the liquid carrier has been removed from the particulate composition; and
   collecting the particulate composition to form the sulfoalkyl ether cyclodextrin composition.

17. The process of claim 16, wherein the combination process is performed in an apparatus having a cylindrical drying chamber.

18. The process of claim 16 further comprising: recycling a portion of the smaller particles in the particulate composition back to the drying chamber at a location between the atomizer and the fluidized bed of particles.

19. The process of claim 16, wherein the process is conducted in a co-current manner.

20. The process of claim 16, wherein the process is conducted in a counter-current manner.

21. The process of claim 16, wherein the process is conducted in a mixed flow manner.

22. The process according to claim 16, wherein the sulfoalkyl ether cyclodextrin is a compound, or a mixture thereof, of the Formula 1:

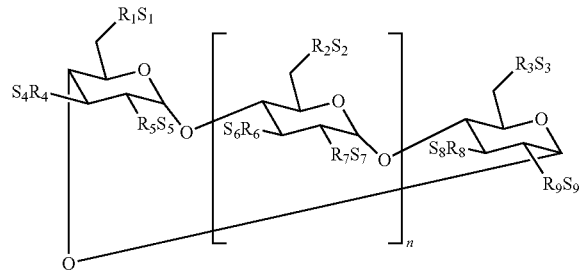

Formula 1 wherein:
   n is 4, 5 or 6;
   $R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$-$R_9$ is independently a —O—($C_2$-$C_6$ alkylene)-$SO_3^-$ group, a —O—$(CH_2)_m SO_3^-$ group wherein m is 2 to 6, —$OCH_2CH_2CH_2SO_3^-$, or —$OCH_2CH_2CH_2CH_2SO_3$); and
   $S_1$, $S_2$, $S_3$, $S_4$, $S_5$, $S_6$, $S_7$, $S_8$ and $S_9$ are each, independently, a pharmaceutically acceptable cation.

23. A composition comprising a sulfoalkyl ether cyclodextrin composition, wherein the sulfoalkyl ether cyclodextrin composition has:
   a. a moisture content below its point of deliquescence;
   b. a bulk density in the range of 0.55 to 0.66 g/cm$^3$; and
   c. a tapped density in the range of 0.49 to 0.75 g/cm$^3$.

24. A composition comprising a sulfoalkyl ether cyclodextrin composition, wherein the sulfoalkyl ether cyclodextrin composition has:
   a. a moisture content below its point of deliquescence;
   b. a bulk density in the range of 0.38 to 0.66 g/cm$^3$; and
   c. a tapped density in the range of 0.66 to 0.75 g/cm$^3$.

* * * * *